(12) United States Patent
Suh et al.

(10) Patent No.: US 11,622,795 B2
(45) Date of Patent: Apr. 11, 2023

(54) MODULAR ROD REDUCTION TOWER AND RELATED METHODS

(71) Applicant: CTL Medical Corporation, Addison, TX (US)

(72) Inventors: Sean Suh, Milltown, NJ (US); Jon Suh, Ambler, PA (US)

(73) Assignee: CTL Medical Corporation, Addison, TX (US)

( * ) Notice: Subject to any disclaimer, the term of this patent is extended or adjusted under 35 U.S.C. 154(b) by 0 days.

(21) Appl. No.: 16/992,955

(22) Filed: Aug. 13, 2020

(65) Prior Publication Data
US 2020/0367946 A1    Nov. 26, 2020

Related U.S. Application Data

(63) Continuation of application No. 16/512,268, filed on Jul. 15, 2019, which is a continuation-in-part of application No. 15/335,026, filed on Oct. 26, 2016, now abandoned.

(60) Provisional application No. 62/758,120, filed on Nov. 9, 2018, provisional application No. 62/257,124, filed on Nov. 18, 2015, provisional application No. 62/247,183, filed on Oct. 27, 2015.

(51) Int. Cl.
*A61B 17/70*    (2006.01)

(52) U.S. Cl.
CPC ...... *A61B 17/7091* (2013.01); *A61B 17/7002* (2013.01); *A61B 17/7086* (2013.01)

(58) Field of Classification Search
CPC .............. A61B 17/708; A61B 17/7083; A61B 17/7085; A61B 17/7086; A61B 17/7091
See application file for complete search history.

(56) References Cited

U.S. PATENT DOCUMENTS

| | | | | |
|---|---|---|---|---|
| 7,744,629 B2* | 6/2010 | Hestad | ............... | A61B 17/7031 |
| | | | | 606/246 |
| 7,846,093 B2* | 12/2010 | Gorek | .................... | A61B 17/86 |
| | | | | 600/206 |
| 8,002,798 B2* | 8/2011 | Chin | .................. | A61B 17/7083 |
| | | | | 606/246 |
| 8,097,026 B2* | 1/2012 | Gorek | .................... | A61B 17/02 |
| | | | | 606/279 |
| 8,137,356 B2* | 3/2012 | Hestad | ............... | A61B 17/7085 |
| | | | | 606/86 A |
| 8,246,538 B2* | 8/2012 | Gorek | ............... | A61B 17/0293 |
| | | | | 600/206 |

(Continued)

FOREIGN PATENT DOCUMENTS

WO        2014184694 A2    11/2014

*Primary Examiner* — Lynnsy M Summit
(74) *Attorney, Agent, or Firm* — Brainspark Associates, LLC

(57) ABSTRACT

A bone fixation system includes a bone fastener and a tower including a frangible or detachably linked distal section with a thread formed on an inner surface thereof, the tower having at least one flexible section and at least one rigid section to accommodate and/or mitigate tower interference and/or collision during surgical procedures. The distal section can desirably be separated and/or detached from the tower to function as a head locking unit of the bone fixation assembly, with the detached distal section capable of accommodating set screws, fixation rods and/or other spinal hardware.

27 Claims, 23 Drawing Sheets

(56) References Cited

U.S. PATENT DOCUMENTS

| | | | | |
|---|---|---|---|---|
| 8,439,923 B2* | 5/2013 | Won | A61B 17/7085 | 606/86 A |
| 8,690,878 B2* | 4/2014 | Marik | A61B 17/7085 | 606/86 A |
| 8,747,407 B2* | 6/2014 | Gorek | B29C 45/14311 | 606/86 A |
| 8,932,210 B2* | 1/2015 | Woods | A61B 17/7085 | 600/201 |
| 8,956,361 B2* | 2/2015 | Davenport | A61B 17/7089 | 606/86 A |
| 9,125,694 B2* | 9/2015 | Butler | A61B 17/7076 | |
| 9,198,692 B1* | 12/2015 | Doose | A61B 17/7086 | |
| 9,655,658 B2* | 5/2017 | Ferreira | A61B 17/708 | |
| 10,004,543 B2* | 6/2018 | Stokes | A61B 17/7085 | |
| 2006/0184178 A1 | 8/2006 | Jackson | | |
| 2007/0106123 A1* | 5/2007 | Gorek | A61B 17/7082 | 600/210 |
| 2008/0077138 A1 | 3/2008 | Cohen | | |
| 2008/0082103 A1* | 4/2008 | Hutton | A61B 17/708 | 606/272 |
| 2008/0114403 A1 | 5/2008 | Kuester | | |
| 2009/0221879 A1* | 9/2009 | Gorek | A61B 17/708 | 600/214 |
| 2009/0222044 A1* | 9/2009 | Gorek | A61B 17/7085 | 606/279 |
| 2010/0174325 A1* | 7/2010 | Won | A61B 17/7037 | 606/305 |
| 2010/0212460 A1* | 8/2010 | Buss | A61B 17/7091 | 81/57.39 |
| 2011/0040328 A1 | 2/2011 | Miller | | |
| 2011/0087293 A1* | 4/2011 | Ferreira | A61B 17/708 | 606/265 |
| 2012/0109208 A1* | 5/2012 | Justis | A61B 17/7089 | 606/264 |
| 2016/0089186 A1 | 3/2016 | Beyer | | |
| 2016/0106480 A1* | 4/2016 | Zhou | A61B 17/7002 | 606/86 A |
| 2017/0273725 A1 | 9/2017 | Miller | | |
| 2018/0353213 A1* | 12/2018 | Biedermann | A61B 17/7032 | |

* cited by examiner

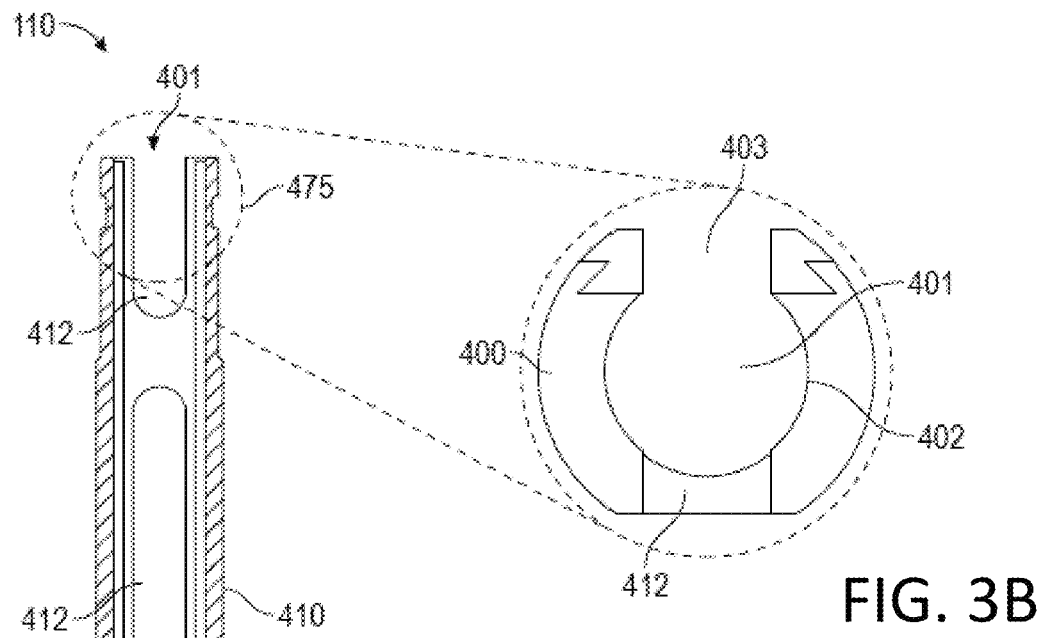
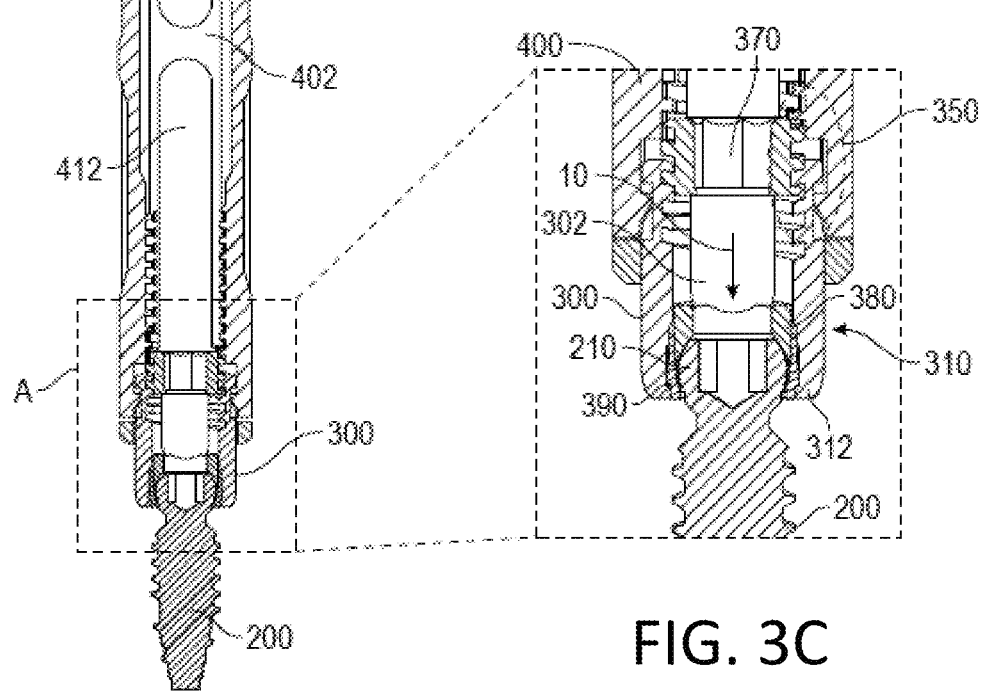
FIG. 3A
FIG. 3B
FIG. 3C

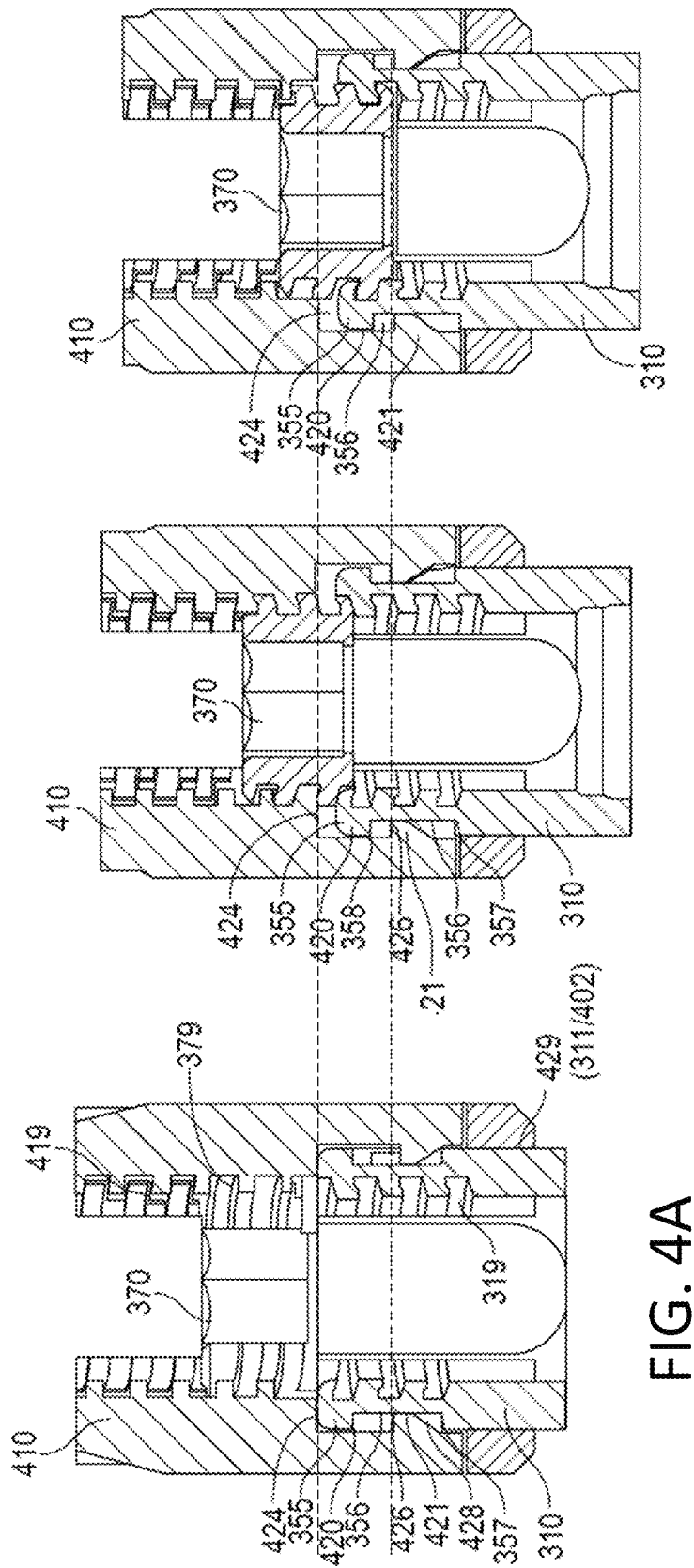

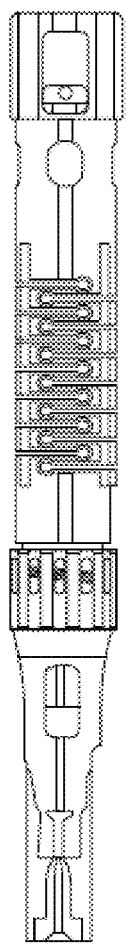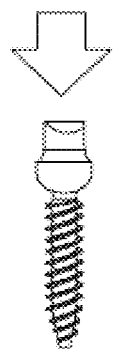
FIG. 10A

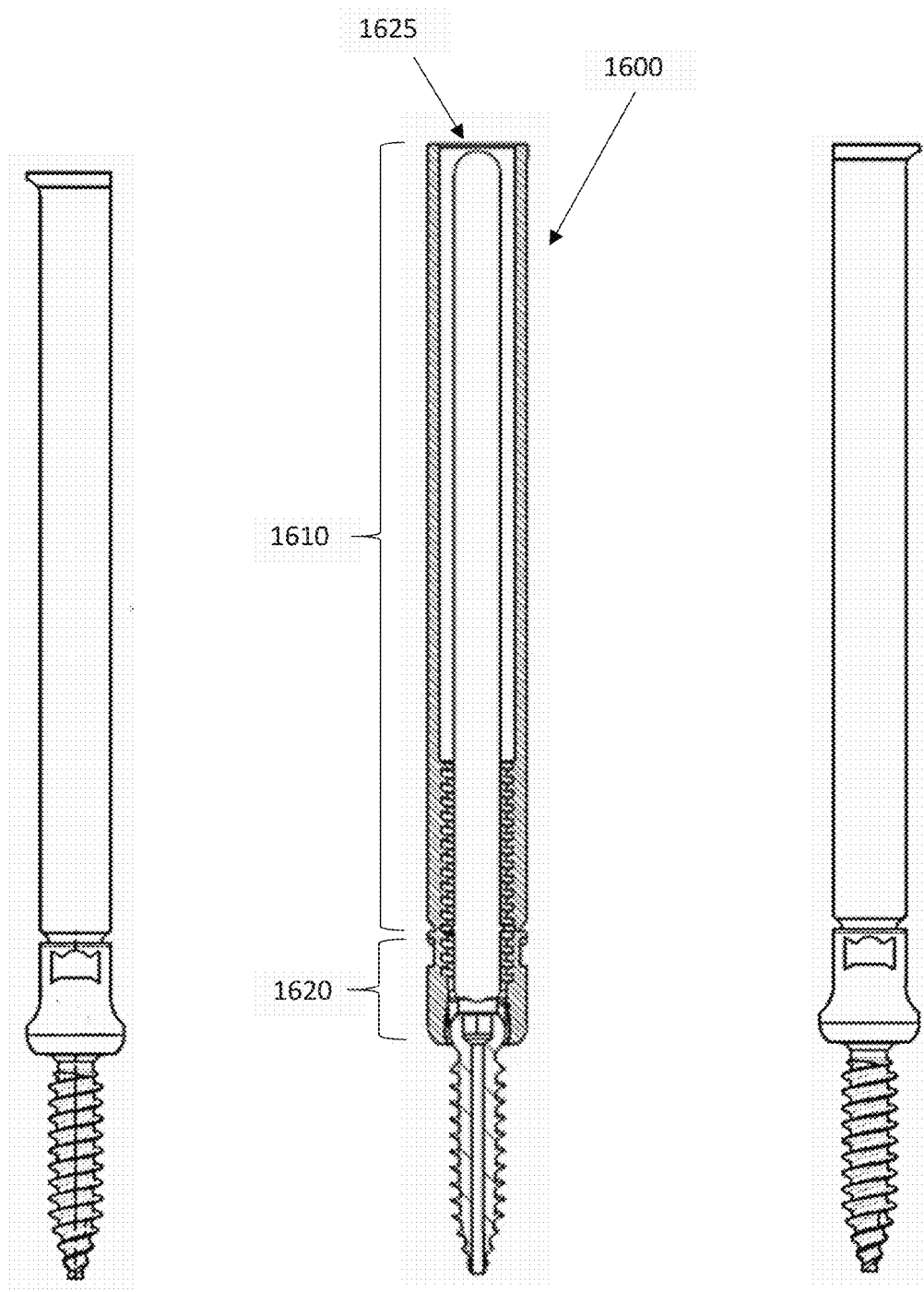

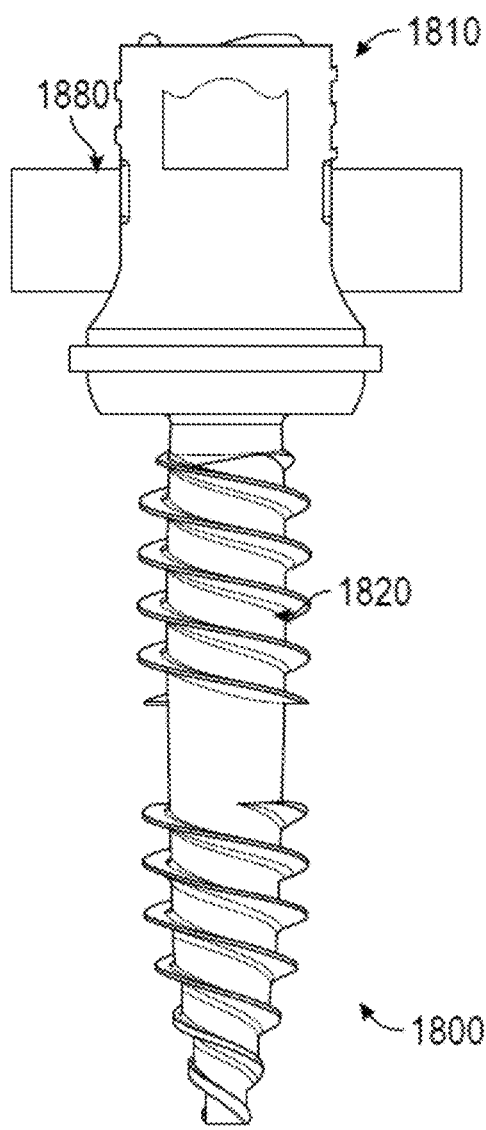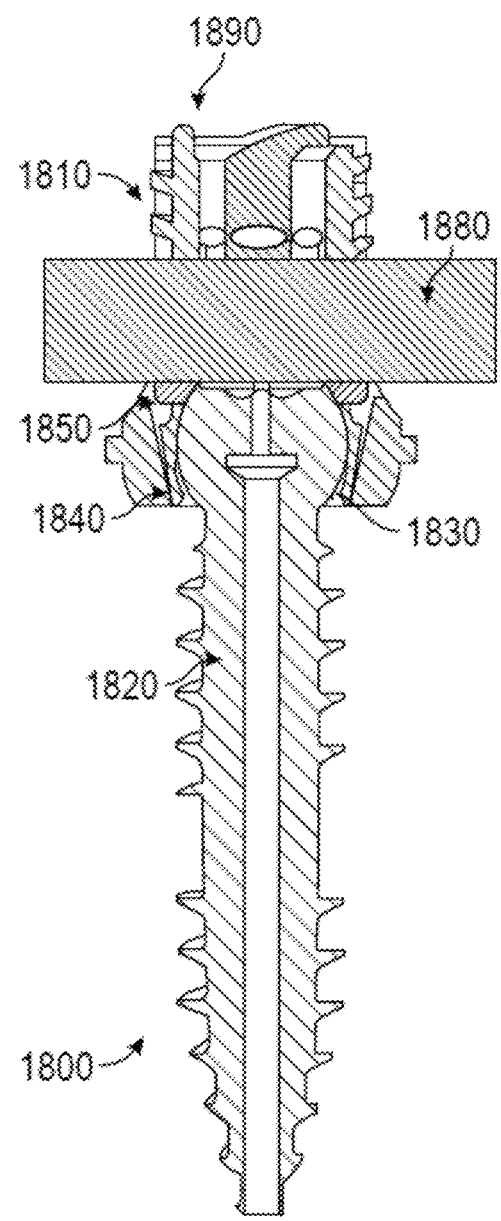
FIG. 18A
FIG. 18B

MODULAR ROD REDUCTION TOWER AND RELATED METHODS

CROSS-REFERENCE TO RELATED APPLICATIONS

This application is a continuation of Utility patent application Ser. No. 16/512,268 filed Jul. 15, 2019, titled "Modular Rod Reduction Tower and Related Methods," which is a continuation-in-part of Utility patent application Ser. No. 15/335,026 filed Oct. 26, 2016, titled "Modular Rod Reduction Tower and Related Methods," which claims priority to and benefit thereof from U.S. Provisional Patent Application No. 62/247,183 filed Oct. 27, 2015, titled "MODULAR DEROTATION TOWER WITH ROD REDUCTION SLEEVE," and U.S. Provisional Patent Application No. 62/257,124, filed Nov. 18, 2015, titled "MODULAR ROD REDUCTION TOWER WITH THREAD PITCH COMPENSATION FEATURE AND METHODS OF USE," each of which are hereby incorporated herein by reference in their entireties.

This application further claims priority to and the benefit of U.S. Provisional Patent Application No. 62/758,120 filed Nov. 9, 2018, titled "Flexible MIS Tower," via Utility patent application Ser. No. 16/512,268, the disclosures of which are each also hereby incorporated herein by reference in their entireties.

FIELD OF THE DISCLOSURE

The present disclosure relates to a bone stabilization system and method, and more particularly to a bone stabilization system and method for implanting within a body of a patient.

BACKGROUND OF THE DISCLOSURE

In mammals, the spinal (or vertebral) column is one of the most important parts. The spinal column provides the main support necessary for mammals to stand, bend, and twist.

In humans, the spinal column is generally formed by individual interlocking vertebrae, which are classified into five segments, including (from head to tail) a cervical segment (vertebrae CI-C7), a thoracic segment (vertebrae TI-TI2), a lumbar segment (vertebrae LI-L5), a sacrum segment (vertebrae SI-S5), and coccyx segment (vertebrate CoI-CoS). The cervical segment forms the neck, supports the head and neck, and allows for nodding, shaking and other movements of the head. The thoracic segment attaches to ribs to form the ribcage. The lumbar segment carries most of the weight of the upper body and provides a stable center of gravity during movement. The sacrum and coccyx make up the back walls of the pelvis.

Intervertebral discs are located between each of the movable vertebra. Each intervertebral disc typically includes a thick outer layer called the disc annulus, which includes a crisscrossing fibrous structure, and a disc nucleus, which is a soft gel-like structure located at the center of the disc. The intervertebral discs function to absorb force and allow for pivotal movement of adjacent vertebra with respect to each other.

In the vertebral column, the vertebrae increase in size as they progress from the cervical segment to the sacrum segment, becoming smaller in the coccyx. At maturity, the five sacral vertebrae typically fuse into one large bone, the sacrum, with no intervertebral discs. The last three to five coccygeal vertebrae (typically four) form the coccyx (or tailbone). Like the sacrum, the coccyx does not have any intervertebral discs.

Each vertebra is an irregular bone that varies in size according to its placement in the spinal column, spinal loading, posture and pathology. While the basic configuration of vertebrae varies, every vertebra has a body that consists of a large anterior middle portion called the centrum and a posterior vertebral arch called the neural arch. The upper and lower surfaces of the vertebra body give attachment to intervertebral discs. The posterior part of a vertebra forms a vertebral arch that typically consists of two pedicles, two laminae, and seven processes. The laminae give attachment to the ligament flava, and the pedicles have a shape that forms vertebral notches to form the intervertebral foramina when the vertebrae articulate. The foramina are the entry and exit passageways for spinal nerves. The body of the vertebra and the vertical arch form the vertebral foramen, which is a large, central opening that accommodates the spinal canal that encloses and protects the spinal cord.

The body of each vertebra is composed of cancellous bone that is covered by a thin coating of cortical bone. The cancellous bone is a spongy type of osseous tissue, and the cortical bone is a hard and dense type of osseous tissue. The vertebral arch and processes have thicker coverings of cortical bone.

The upper and lower surfaces of the vertebra body are flattened and rough. These surfaces are the vertebral endplates that are in direct contact with the intervertebral discs. The endplates are formed from a thickened layer of cancellous bone, with the top layer being denser. The endplates contain adjacent discs and evenly spread applied loads. The end plates also provide anchorage for the collagen fibers of the disc.

FIG. 1 shows a portion of a patient's spinal column 2, including vertebra 4 and intervertebral discs 6. Each disc 6 forms a fibrocartilaginous joint between adjacent vertebrae 4, allowing relative movement between adjacent vertebrae 4. Beyond enabling relative motion between adjacent vertebrae 4, each disc 6 acts as a shock absorber for the spinal column 2.

As noted earlier, each disc 6 comprises a fibrous exterior surrounding an inner gel-like center which cooperate to distribute pressure evenly across each disc 6, thereby preventing the development of stress concentrations that might otherwise damage and/or impair vertebrae 4 of spinal column 2. Discs 6 are, however, subject to various injuries and/or disorders which may interfere with a disc's ability to adequately distribute pressure and protect vertebrae 4. For example, disc herniation, degeneration, and infection of discs 6 may result in insufficient disc thickness and/or support to absorb and/or distribute forces imparted to spinal column 2. Disc degeneration, for example, may result when the inner gel-like center begins to dehydrate, which may result in a degenerated disc 8 having decreased thickness. This decreased thickness may limit the ability of degenerated disc 8 to absorb shock which, if left untreated, may result in pain and/or vertebral injury.

Thus, when a spinal abnormality occurs, the abnormality can cause severe pain or damage to the nervous system. The abnormality may also severely limit movement of the spinal column. The abnormality may be the result of, for example, trauma, degenerative disc disease, degenerative bone disease, or the like.

There exists an unfulfilled need for improved bone stabilization devices, associated systems, and methodologies related thereto. Since recovery from spinal surgery is typically a long and arduous process that places severe restrictions on patient mobility, a continuing need exists for systems and methodologies that improve patient recovery and reduce recovery time after surgery.

SUMMARY OF THE DISCLOSURE

According to an aspect of the disclosure, a bone fixation system includes a bone fastener, a tower including a first thread formed on an inner surface at a first end thereof, a coupling assembly connected to the bone fastener and the first end of the tower. The coupling assembly includes a coupling unit including a second thread formed on an inner surface at an upper portion thereof and adjoining the first thread, and a set screw including a third thread configured to mate with the first thread and the second thread. The coupling unit is configured to compensate a thread pitch mismatch between the first thread and the second thread.

The bone fastener includes a polyaxial pedicle screw having a head and a screw shaft extending from the head.

The coupling assembly further includes a cavity that receives and holds a portion of the bone fastener.

The coupling assembly further includes a channel formed by a pair of upper inner walls of the coupling unit.

The bone fixation device further includes a fastener connector having a portion that seats within the channel.

The tower further includes a coupling guide formed around an inner surface at the first end portion thereof.

The coupling unit further includes a coupling lip formed on an outer surface of an upper portion thereof that seats in the coupling guide of the tower.

The coupling guide is formed by a recessed surface extending between an upper recess surface and a lower recess surface, the recess surface being wider than the coupling lip of the coupling unit.

The coupling unit travels in a direction in response to a force applied by the set screw when the first thread and the second thread are misaligned.

The third thread of the set screw mates with the second thread of the coupling unit when a thread pitch of the first thread is aligned with a thread pitch of the second thread.

According to another aspect of the disclosure, a bone fixation system includes a tower having a tower body that includes an internal tower thread, and a thread pitch compensator. The thread pitch compensator substantially matches the pitch of the tower thread to a pitch of a thread in a coupling body to facilitate progression of a set screw from the tower thread into and along the thread in the coupling body.

The thread pitch compensator includes a coupling guide that holds and guides a coupling lip on the coupling body.

The thread pitch compensator includes a tower lip.

The thread pitch compensator includes a stop that limits travel of the coupling lip in the coupling guide.

The coupling guide allows the coupling lip to move in either direction along a longitudinal axis of the tower.

According to yet another aspect of the disclosure, a bone fixation system includes a hollow shell body having an opening at a first end portion thereof, and a derotation tower that envelopes a tower of a bone fastener when inserted into the hollow shell body via the opening of the hollow shell body.

The hollow shell body includes a grip portion having a diameter greater than that of the first end portion thereof.

The bone fixation system further includes a crosslink unit that removably affixes to a second end portion of the hollow shell body.

A length of the crosslink unit is adjustable.

The crosslink unit includes a bent end portion that removably affixes to the second end portion of the hollow shell body.

Additional features, advantages, and embodiments of the disclosure may be set forth or apparent from consideration of the detailed description and drawings. Moreover, it is to be understood that both the foregoing summary of the disclosure and the following detailed description are exemplary and intended to provide further explanation without limiting the scope of the disclosure as claimed.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to help explain the principles of the disclosure. No attempt is made to show structural details of the disclosure in more detail than may be necessary for a fundamental understanding of the disclosure and the various ways in which it may be practiced. In the drawings:

FIG. 3A shows an example of a bone fixation device, constructed according to the principles of the disclosure;

FIGS. 3B and 3C show enlarged views of portions of the bone fixation device in FIG. 3A;

FIGS. 4A, 4B and 4C show enlarged views of a connection portion of the bone fixation system in FIG. 3A;

FIGS. 10A and 10B depict attachment of a spinal instrument having a flexible zone being attaching to a spinal fixation element;

FIGS. 16A through 16C depict another alternative embodiment of a tower body with an integrated detachable tip portion;

FIGS. 18A and 18B depict front plan and cross-sectional views, respectively, of one embodiment of an exemplary fixation element incorporating a tip portion which engages with a bone fastener in the form of a polyaxial pedicle screw.

Figure 1:
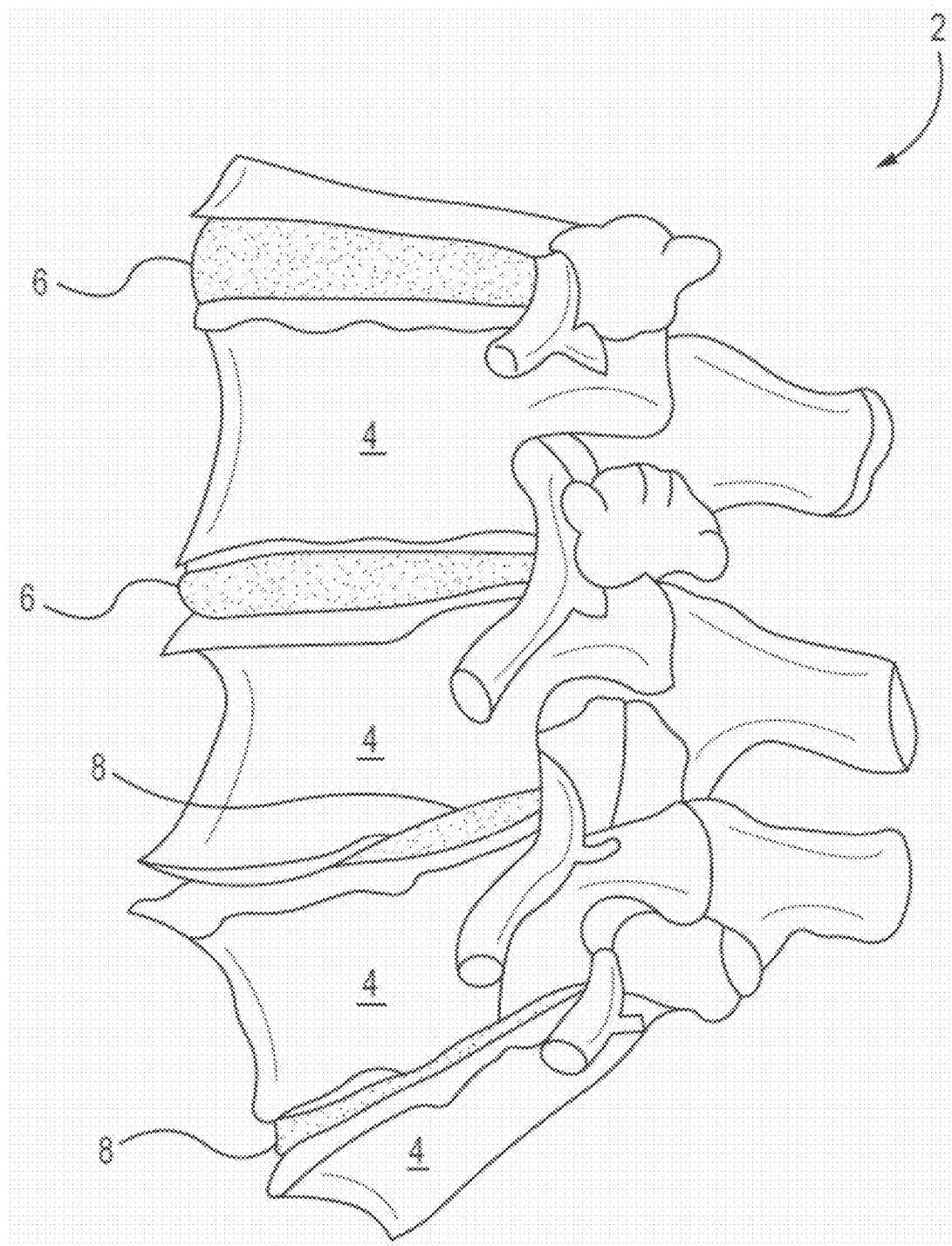
FIG. 1 illustrates a portion of a patient's spinal column.

The present disclosure is further described in the detailed description that follows.

DETAILED DESCRIPTION OF THE DISCLOSURE

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

Referring to FIG. 1, when a spinal abnormality occurs in the spinal column 2, the abnormality can cause severe pain or damage to the nervous system, and the abnormality may limit movement of the spinal column. As noted earlier, the abnormality may be the result of, for example, trauma, degenerative disc disease, degenerative bone disease, or the like.

According to an aspect of the disclosure, the abnormality may be treated by affixing bone fasteners (such as, for example, bone screws or hooks) to one or more vertebrae and connecting the bone fasteners to a fastener connector (such as, for example, a rod, a curved rod, a straight rod, a wire, a cross-connector rod, a cross-connector wire, or the like). The fastener connector may be aligned with the longitudinal axis of the spinal column 2 to immobilize the spinal segment (e.g., adjacent vertebrae 4) with respect to each other. For instance, the bone fasteners may comprise bone screws that are screwed into pedicles of vertebrae 4 and coupled to at least one fastener connector that may include an elongated rod. The pedicles, which consist of a strong shell of cortical bone and a core of cancellous bone, provide the strongest point of attachment of a spine and, therefore, the greatest resistance against bone-metal junction failure. The bone fasteners may be positioned so as to traverse all three columns of the vertebrae, thereby providing ventral and dorsal stability in the spinal column 2.

Figure 2:
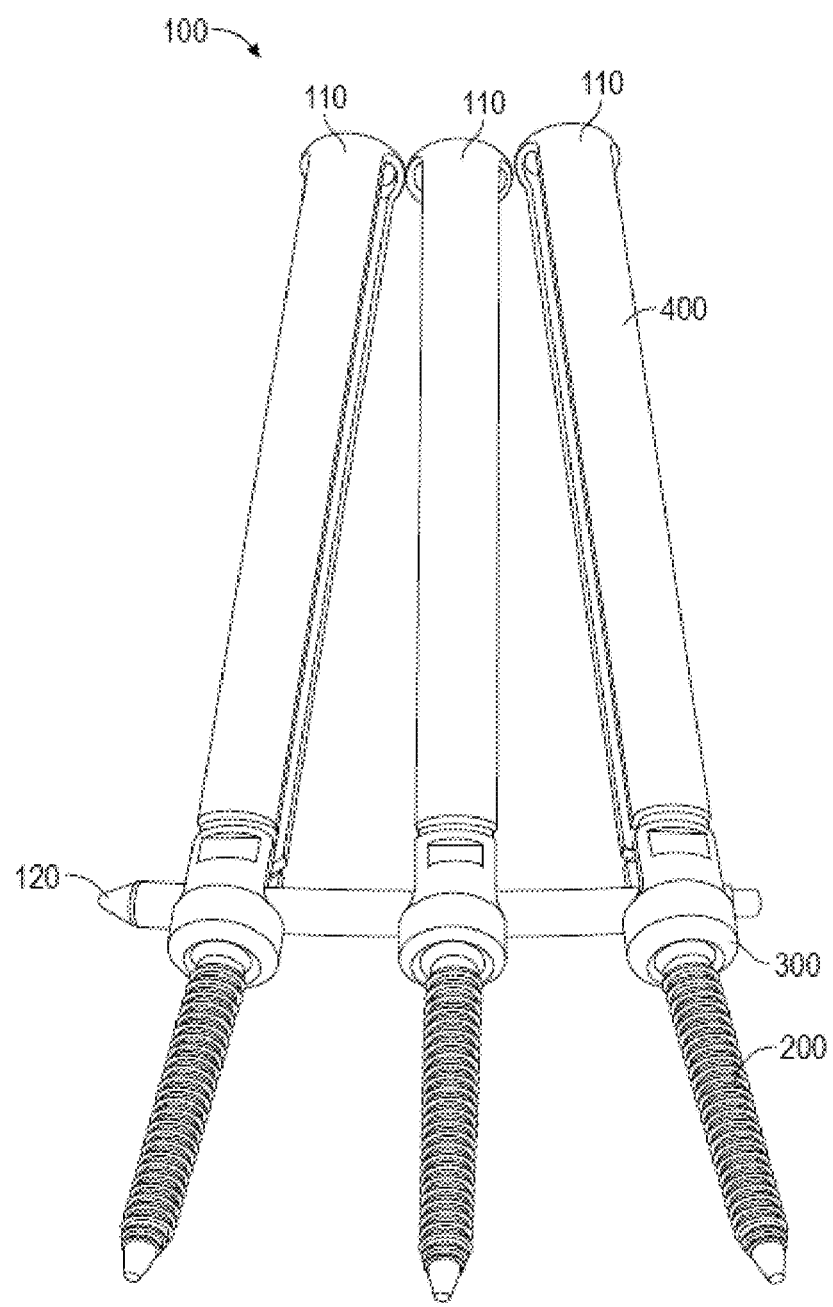
FIG. 2 shows an example of a bone fixation system that may be implanted in a spinal column, according to the principles of the disclosure.

FIG. 2 shows an example of a bone fixation system 100 that may be implanted in the spinal column 2 (shown in FIG. 1) of a patient's body. Once implanted in a patient's spinal column 2, the bone fixation system 100 may properly position, stabilize and promote fusion in a portion of the spinal column 2, such as, for example, two or more adjacent vertebrae. The bone fixation system 100 may comprise any number of bone fixation devices 110 and fastener connectors 120. Each bone fixation device 110 may include a bone fastener assembly 200/300 and a tower 400. FIG. 2 shows one non-limiting embodiment wherein the bone fixation system 100 comprises three bone fixation devices 110 and a single fastener connector 120 connecting to the bone fastener assemblies 200/300 of all three of the bone fixation devices 110. The bone fastener assembly 200/300 includes a bone fastener 200 and a coupling assembly 300, collectively referred to as bone fastener assembly 200/300. According a non-limiting embodiment, the bone fastener 200 in the bone fixation device 110 may comprise a poly-axial pedicle screw 200.

Figure 3D:
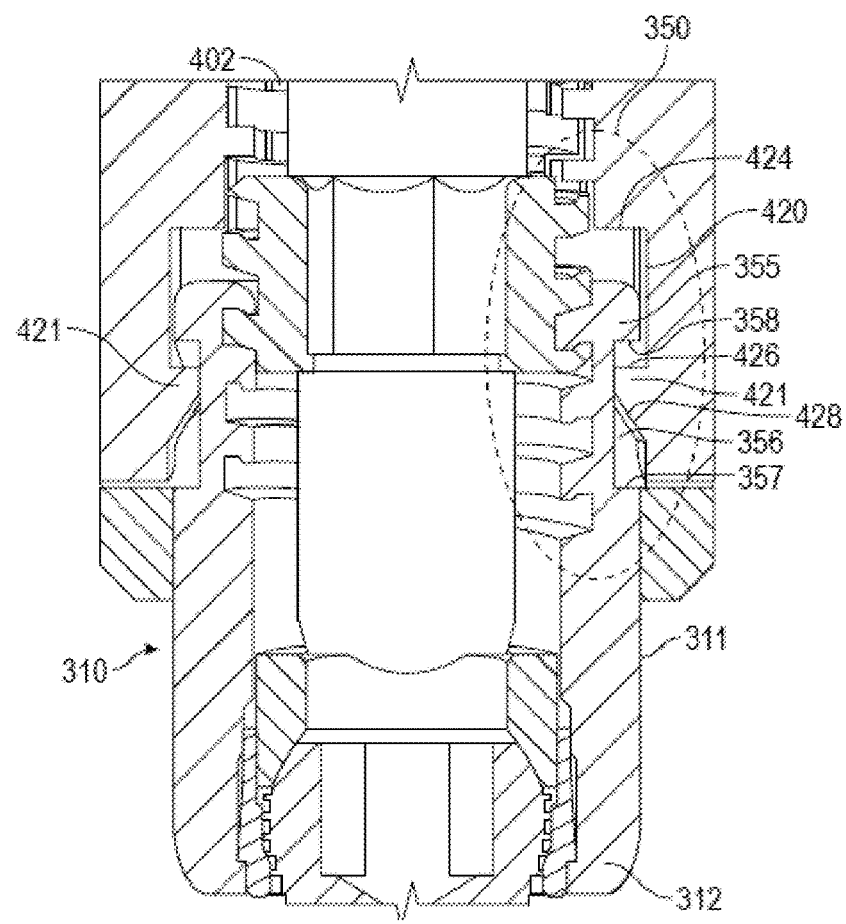
FIG. 3D shows an enlarged cross-section cut view of an example of a thread pitch compensation feature in a bone fixation device, according to the principles of the disclosure.
Figure 3E:
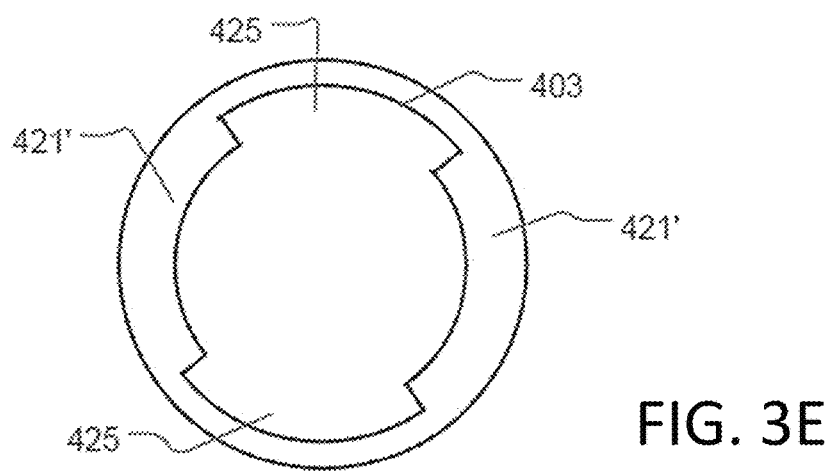
FIG. 3E shows a bottom view of an example of a tower, constructed according to principles of the disclosure.

FIGS. 3A to 3E show various views of the bone fixation device 110 and/or the tower 400, according to principles of the disclosure. FIG. 3A shows a cross-section cut view of a non-limiting embodiment of the bone fixation device 110, constructed according to the principles of the disclosure; FIG. 3B shows a top view of the bone fixation device 110; FIG. 3C shows an enlarged cross-section cut view of a connection portion A of the bone fixation device 110; FIG. 3D shows an enlarged cross-section cut view of a non-limiting embodiment of a thread pitch compensator 350 in the bone fixation device 110; and FIG. 3E shows an example of a receiving end of the tower 400.

Referring to FIG. 3A, the tower 400 has a tower body 410 that may be removably attached to the coupling assembly 300. The tower body 410 may have a cylindrical or tube-like shape with a tool insertion channel 401 formed therein by the inner walls 402 of the tower body 410. The tool insertion channel 401 may be used to receive and guide a tool, such as, for example, a screw driver (not shown), facilitating delivery of an end of the tool (not shown) to the bone fastener 200 (for example, the head of the polyaxial pedicle screw) and/or a set screw 370, so as to allow manipulation (e.g., tightening or loosening) of the bone fastener 200 and/or the set screw 370.

As seen in FIG. 3B, when viewed from above, the walls of the tower body 410 have a tower end 475 that may have a semi-closed (or semi-open) shape, such as, for example, a "C" shape having an open channel 403 formed in the tower body 410. The channel 403 may be provided to allow a portion of a tool (not shown) being inserted in or through the tool insertion channel 401 to protrude from the tower body 410, or to deploy or retrieve a device such as, for example, a fastener connector 120 (shown in FIG. 2) along the channel 401 using, for example, a rod inserter tool (not shown). For instance, the tool (not shown) and fastener connector 120 may be delivered along the tool insertion channel 401 of the tower body 410, and when the tool end (not shown) is positioned in a predetermined position, the fastener connector 120 may be pivoted outward and extended from the tower body 410 (via the channel 403) to be seated in or inserted into the coupling assemblies 300 in the bone fixation system 100 (shown in FIG. 2). The walls of the tower body 410 may include one or more openings (or cutouts) 412 that may run along less than the entire length of the tower 400. Alternatively, the opening (or cutout) may run along the entire length of the tower 400.

Alternatively, the tower body 410 may be a closed type (not shown) that has a closed loop all around, or an open type (not shown) that may have multiple open channels (or cutouts) 403 formed on opposite sides of the tower 400. The tower body 410 may include openings (or cutouts) 412, which may run along the entire length of the tower 400. Alternatively, the openings (or cutouts) 412 may run along less than the entire length of the tower 400. The length of one opening (or cutout) 412 may be the same as, or differ from the length of the other opening (or cutout) 412.

As seen in FIG. 3C, the coupling assembly 300 may include a coupling body (or unit) 310 and a set screw 370. The coupling assembly 300 may further include a first (or upper) inner ring 380 and a second (or lower) inner ring 390. The coupling body 310 may have a tulip-shape, or a "U"-shape at a first (or upper) end, so as to allow the fastener connector 120 (shown in FIG. 2) to be positioned within a channel 302, which may be formed by upper inner walls of the coupling body 310. The width of the channel 302 may be substantially the same as, or greater than the width (or diameter) of the fastener connector 120.

The coupling body 310 may have a cavity at its opposite (or lower) end. The cavity may be formed by the inner walls of the lower portion of the coupling body 310. The coupling body 310 may further include a stop against which a portion of the upper surface of the upper inner ring 380 may rest. The coupling body 310 may further include a lip portion 312 that may protrude inward and serve as a stop to limit downward movement of the lower inner ring 390 from the cavity. The cavity may be configured to receive and hold the first (upper) inner ring 380 and the second (lower) inner ring 390, partially or entirely within the cavity.

In the embodiment where the bone fastener 200 includes a polyaxial pedicle screw, when assembled the first inner ring 380 and second inner ring 390 may form a further cavity that holds a head portion 210 of the polyaxial pedicle screw. The first inner ring 380 and the second inner ring 390 are designed such that when a force is applied in the direction of the arrow 10 (e.g., a force that is substantially perpendicular to the plane of the upper surface of the inner ring 380), the volume of the cavity that holds the head portion 210 of the bone fastener 200 is compressed or reduced, thereby securely engaging and holding the head portion 210 of the bone fastener 200 by the inner walls of the first inner ring 380 and/or second inner ring 390. In the example shown in FIG. 3C, the force is applied to the upper surface of the inner ring 380 by the fastener connector 120 (shown in FIG. 2), which may be forced to move in the direction of the arrow 10 by the set screw 370, as the set screw 370 is turned and driven toward the first inner ring 380. The design of the coupling assembly 300 is configured such that the upper inner ring 380 may transfer load from the fastener connector 120 to the top surface of the head portion 210 of the bone fastener 200. The design upgrades line contact into surface contact for stable seating of the fastener connector 120 and load transfer.

Referring to FIG. 3C and FIG. 3D, the bone fixation device 110 may include a thread pitch mismatch compensator 350. As seen in FIG. 3D, according to a non-limiting embodiment, the thread pitch mismatch compensator 350 includes a coupling guide 420 that receives and guides a coupling lip 355 of the coupling body 310. The coupling guide 420 may be configured to receive and guide known coupling body housings, so that the tower 400 may be attached to existing bone fastener assemblies having various sizes and configurations. The coupling guide 420 may be formed in the inner wall 402 of the tower body 410. The coupling guide 420 may have an annular shape that may be cut from, or formed in a section of the inner wall 402 of the tower body 410. For instance, the coupling guide 420 may be formed in a 360° section of the inner wall 402 of the tower body 410, formed along and around the inner wall 402 of the tower body 410 and substantially perpendicular to the longitudinal axis of the tower body 410. The coupling guide 420 may be formed in less than a 360° section of the inner wall 402, or in multiple sections of the inner wall 402. The coupling guide 420 is configured to receive, hold, and guide a coupling lip 355 on the coupling body 310, allowing the coupling lip 355 to travel in the coupling guide 420 in either direction along the longitudinal axis of the tower body 410.

The coupling guide 420 may include a stop 424 and a tower lip 421 that may function to limit the travel of the coupling lip 355 at each end of the coupling guide 420. The stop 424 may include a wall surface that is substantially perpendicular to the longitudinal axis of the tower body 410. The tower lip 421 may include a first wall 426 that has a surface that is substantially perpendicular to the longitudinal axis of the tower body 410 and faces the coupling guide 420. The tower lip 421 may include a second wall 428 that may have an angled or tapered surface. The surface angle of the wall 428 may be, for example, between 5° and 90° with respect to the longitudinal axis of the tower body 410, and preferably between 30° and 60°. The surface angle of the wall 428 may be less than 5°, or more than 90° with respect to the longitudinal axis of the tower body 410. The surface of the wall 428 may be angled or tapered to allow the coupling lip 355 of the coupling body 310 to be forced by, and guided along the angled surface of the wall 428, past an edge of the wall 426, and allowed to be snapped into position in the coupling guide 420.

The tower lip 421 may be annular shaped and may be formed 360° around the inner wall 402 of the tower body 410. Alternatively, the tower lip 421 may be less than 360° and may be formed along one or more portions of the inner wall 402 of the tower body 410.

The upper portion of the coupling body 310, including the coupling lip 355, may be configured to be compressible, thereby allowing the perimeter of the coupling lip 355 to be reduced upon application of an external inward force (e.g., a force applied in the direction of the center of the coupling lip 355 by the surface of the wall 428), and to expand to a default configuration in the absence of an external force (shown in FIG. 3C).

Alternatively (or additionally), the bone fastener receiving end of the tower 400 (portion A, shown in FIG. 3A) may be made of a material that may flex (or stretch) satisfactorily under force and revert to a default configuration (shown in FIG. 3C) after the force is removed. The force may be introduced by the outer surfaces of the coupling lip 355 when the coupling lip 355 is inserted into the coupling guide 420.

FIG. 3E shows an example of a bone fastener assembly receiving end of the tower 400 having a tower lip 421 formed as a pair of tower lip segments 421'. As seen, the tower lip segments 421' may be positioned opposite each, with spaces 425 being left open therebetween. The lengths of the tower lip segments 421' may be the same, or one tower lip segment 421' may be longer than the other. The lengths of the spaces 425 may be substantial identical or different.

According to a non-limiting embodiment of the tower 400, the lengths of the tower lip segments 421' may be substantially the same as, or less than the width of the channel 302 in the coupling body 310. In this embodiment, the coupling lip 355 may be formed as a pair of coupling lip segments provided on each of the pair of upper portions of the coupling body 310 that form the U-shape and channel 302 therebetween. During assembly, the pair of coupling lip segments provided on the pair of upper portions of the coupling 310 may be aligned with the spaces 425 and the coupling body 310 inserted into the tower end (shown in FIG. 3E) until upper surfaces of the coupling lip 355 contact (or nearly contact) the stop 424 of the coupling guide 420. Then, the tower body 421 (and/or coupling body 310) may be rotated until the coupling lip segments substantially overlap with the tower lip segments 421', thereby securing the coupling lip 355 in the coupling guide 420.

According to a further non-limiting embodiment of the tower 400, the tower lip 421 may be configure as a single 360° thread (not shown) that may allow the coupling lip 355 to be inserted in and guided by the thread into the coupling guide 420 when the coupling body 310 (or tower body 410) is rotated at least one complete turn with respect to the tower body 410 (or coupling body 310). The thread maybe less than 360° or greater than 360°.

The coupling body 310 may include one or more recessed grooves 356. The groove 356 may be formed in the outer wall 311 of the coupling body 310. The groove 356 may have a substantially flat, an annular, or a semi-annular shape that may be cut from, or formed in the coupling body 310. In a non-limiting embodiment of the coupling body 310 having tulip (or U-shaped) upper portions, at least one groove 356 may be provide in the outer wall 311 of each upper portion near the coupling lip segment that is provided at upper end of the coupling body 310.

According to another non-limiting embodiment of the coupling body 310, the groove 356 may be formed in a 360° section of the outer wall 311, formed along and around the entire perimeter of the outer wall 311. The groove 356 may be formed substantially perpendicular to the longitudinal axis of the coupling body 310 and/or the tower body 410. The groove 356 may be formed in less than a 360° section of the outer wall 311, as discussed herein with respect to the embodiment shown in FIG. 3E. The groove 356 may be configured to receive, hold, and guide the tower lip 421 (or tower lip segment 421'), allowing the tower lip 421 to travel in either direction in the groove 356, along the longitudinal axis of the coupling body 310 and/or tower body 410. The tower lip 421 may also be permitted to travel in and along the groove 356 in a direction that is substantially perpendicular to the longitudinal axis of the coupling body 310, such as, for example, when the coupling body 310 is rotated with respect to the tower body 410.

The groove 356 may include one or more walls 357, 358. The walls 357 and/or 358 may function to limit travel of the tower lip 421 in the groove 356 along the longitudinal axis of the tower body 410. According to a non-limiting embodiment, the wall 358 may be a portion of the coupling lip 355, the surface of which may be formed to face the groove 356 and be substantially perpendicular to the longitudinal axis of the coupling body 310. The wall 357 includes a surface that may be substantially perpendicular to the longitudinal axis of the tower body 421 and facing the groove 356.

FIGS. 4A, 4B and 4C show three enlarged cross-sectional cut views of the thread pitch mismatch compensator 350 at three different stages of implementation to compensate the thread pitch mismatch and misalignment that may otherwise occur between the threads 319, 419 of the coupling assembly 300 and the tower 400, respectively.

FIG. 4A shows an example of a stage of implementation of the thread pitch mismatch compensator 350, wherein thread misalignment and thread pitch mismatch between the inner surfaces of the coupling body 310 and the tower 400. It is understood that, without the thread pitch mismatch compensator 350, the configuration in FIG. 4A would block any further downward movement of the set screw 370. However, the thread mismatch compensator 350 compensates for the thread pitch mismatch by allowing the coupling body 310 to move with respect to the tower body 410 (shown in FIGS. 4A-4C) until such time as the threads 319 of the coupling body 310 are matched to the threads 379 of the set screw 370, allowing the set screw to engage and progress along the threads 319 of the coupling body 310.

As seen in FIG. 4B, with the coupling guide 420 that allows movement of the coupling body 310 with respect to the tower body 410, when a rotational force is applied to move the set screw 370 further downward, the coupling body 310 may be pushed and move downward by the set screw 370. The coupling lip 355 may contact the surface wall of the coupling guide 420 and be guided along the coupling guide 420, such that the threaded inner surface of the coupling body 310 does not move laterally when the coupling body 310 is pushed down by the set screw 370. The coupling body 310 may be further guided by the contact 429 between the outer wall 311 and the inner wall 402 of the tower body. The coupling body 310 may continue to move until the threads 379 on the set screw 370 are aligned with and match the threads 319 in the coupling body 310 (shown in FIG. 4B). After the threads 379 and 319 match, the set screw 370 may engage and proceed along the thread 319 and, thereby, inner walls of the coupling body 310.

As seen in FIG. 4C, at some point of the rotational and downward movement of set screw 370, the thread pitch of the threads 379 and 319, as well as the thread pitch of the threads 419 in the tower 400, become aligned and the set screw 370 may begin to mate with the thread 319 of the coupling body 310. The set screw 370 may then make a transition from the tower body 410 and into the coupling body 310.

Accordingly, the bone fixation device 110 may be constructed to compensate the thread pitch mismatch between the threads of the coupling assembly 300 and the tower 400, which can eliminate cross threading therebetween. No additional parts are required to implement the thread pitch mismatch compensation features, and, therefore, the size and number of moving parts of the bone fixation device 110 may be minimized, thereby facilitating minimally invasive surgery (MIS) procedures. Also, the same tower 400 may be interchangeably used with bone fastener assemblies 200/300 having different sizes and/or configurations to form the bone fixation device 110.

A method of implanting the bone fixation system 100 (shown in FIG. 2), and more particularly, a plurality of bone fixation devices 110 and fastener connectors 120 will now be described. Initially, the patient may be placed in a prone position on a radiolucent table and draped in the usual manner. Using imaging, such as, for example, fluoroscopy and preoperative imaging, a location may be determined for each incision and the incision made. After the necessary incision is made, a targeting needle (not shown) may be inserted through the dissected tissue to the level of a target pedicle. After confirming that the targeting needle is properly placed and has the correct trajectory, the targeting needle may be tapped into the vertebral body until depth is satisfactory. The trajectory and depth of the targeting needle should be repeatedly confirmed using the imaging (e.g., fluoroscopy) as the needle is being inserted.

After the needle is inserted to its final position, an inner stylus (not shown) may be removed from the needle and a K-wire inserted in its place to an appropriate depth. The targeting needle may then be removed while carefully maintaining control of the depth of the guide wire. The foregoing steps may be repeated for each of the remaining pedicles.

Next, a dilator (not shown) may be inserted over the guide wire, keeping the guide wire steady in the process. Once properly placed, the starter dilator tube (not shown) may be removed, leaving the second (not shown) and final dilator (not shown) in place. An appropriately sized cannulated tap (not shown) may be inserted over the guide wire and through the second dilator. The cannulated tap may be tapped to desired length while maintaining the position and depth of the guide wire. Imaging may be used to verify that the tap is following the trajectory of the guide wire during insertion.

At this point, the correct size and/or configuration of the bone fastener assembly 200/300 (e.g., polyaxial pedicle screw assembly) may be selected for the particular procedure.

Referring to FIGS. 3A and 3C, after the appropriately sized bone fastener assembly 200/300 is selected for the procedure, a universal tower 400 may be attached to the bone fastener assembly 200/300 to form the bone fixation device 110. An advantage of using a universal tower 400 according to the principles of the disclosure is that only a single size of tower 400 could be stocked for various sizes and/or configurations of bone fastener assemblies 200/300 (such as, for example, polyaxial pedicle screw assemblies). The tower 400 is bone fastener assembly-agnostic. In other words, the tower 400 may be used with different sizes and/or configurations of bone fastener assemblies 200/300 (such as, for example, generic pedicle screw assembly housings), including bone fastener assemblies 200/300 to be used for MIS or reduction procedures.

If the bone fixation device 110 is not preassembled, it may be assembled using the selected bone fastener assembly 200/300 with the tower 400 constructed according to the principles of the disclosure.

Holding the base of the bone fastener 200 in one hand, and a portion of the tower body 410 at the receiving end of the tower 400 (portion A, shown in FIG. 3A) in the other hand, the bone fastener assembly 200/300 may be pushed into the receiving end of the tower body 410 (portion A in FIG. 3A), such that the coupling lip 355 of the coupling body 310 is forced to compress under force of the angled wall 428 until it passes an edge of the wall 426, at which point the coupling lip 355 will be in the coupling guide 420 and may snap to its default configuration (shown in FIG. 3C). The tower body 410 may be made of a material that may permit the tower body 410 to flex, so as to facilitate insertion of the coupling lip 355 past the tower lip 421 and into the coupling guide 420. In this latter regard, the coupling body 310 need not be flexible.

Figure 8A:
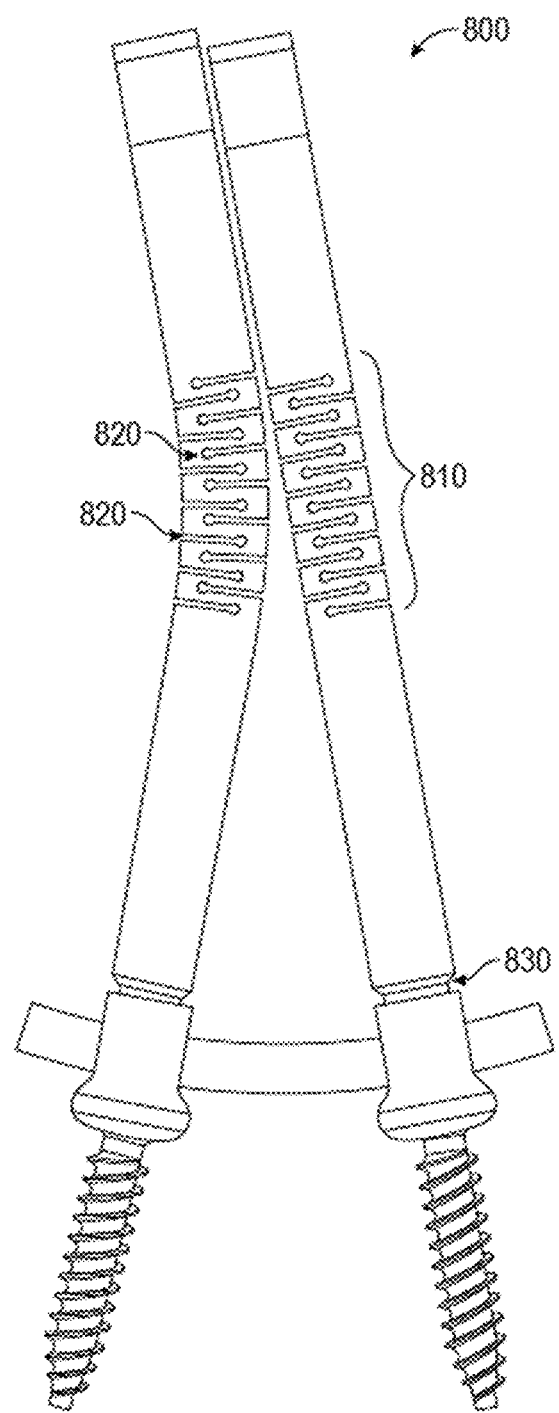
FIG. 8A depicts an exemplary embodiment of tower bodies that incorporate one or more flexible portions.
Figure 8B:
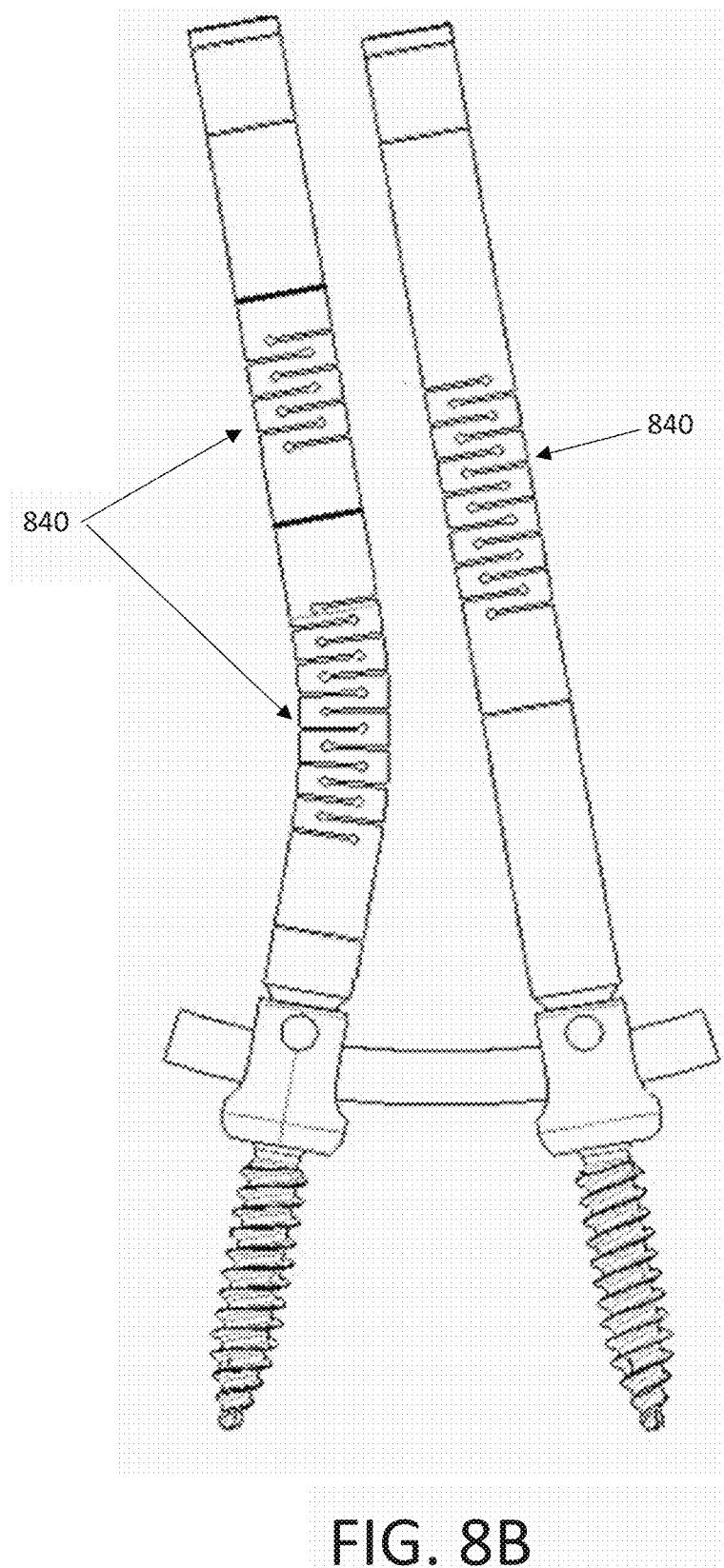
FIG. 8B depicts an alternative embodiment of tower bodies that incorporate one or more flexible portions, including a modular tower incorporating a removable and/or reconfigurable flexible section.

In at least one exemplary embodiment, such as depicted in FIGS. 8A and 8B, one or more of the tower bodies 800 may incorporate one or more flexible portions 810, which in various embodiments may comprise a section or subsection of a tower body that has been "weakened" or otherwise rendered more flexible (i.e., by machining and/or material removal, for example) than other portions of the tower body 800. To make the tower housing more flexible, a series of slit cut patterns 820 or similar features (including other partial material removal operations) can be made along one or more regions of the tower wall structure, such as along the middle region of the tower as shown in FIG. 8A, where a center of curvature of the flexible section can exist. In at least one exemplary embodiment, a desired center of curvature (or a distance from the rod to the center of the slit pattern) can range from 50 mm to 250 mm. The tower element may be continuous, or may comprise two or more (i.e., a series) individual interlocking sections, desirably with a modular feature 830 for engaging directly with a top portion of a pedicle screw housing, including attachment to a low top pedicle screw housing in some embodiments.

As depicted in FIG. 8B, the tower bodies can include one or a plurality of flexible portions 840, including flexible portions of differing lengths, sizes and/or positions, if desired. It some embodiments, the flexible portions can include a modular segment, which can be attached to a desired portion of the tower at virtually any position along its length (not shown).

Figure 9A:
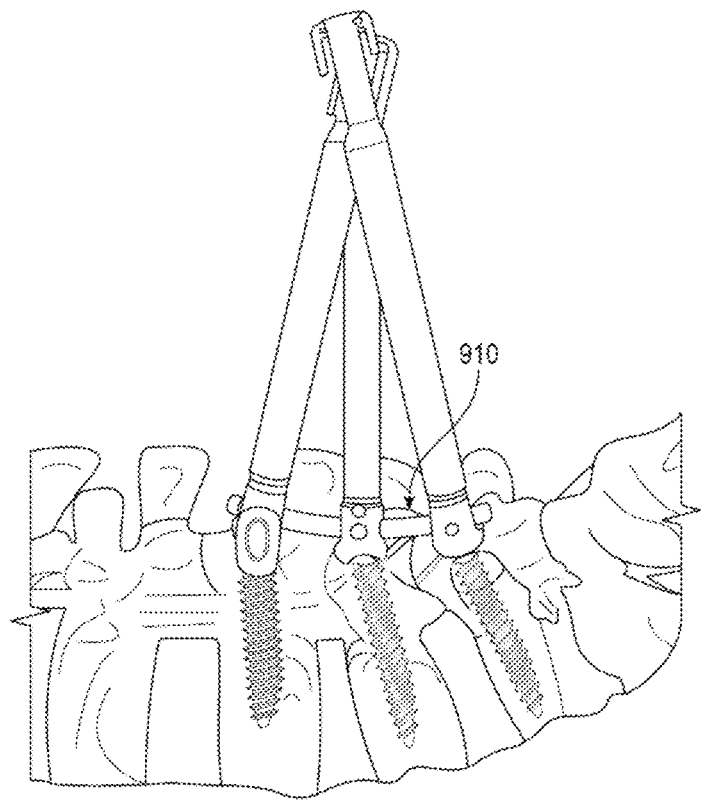
FIG. 9A depicts an exemplary interference or collision of tower bodies in a spine analog.

During many surgical procedures, tower collision or other tool interference can be a common occurrence due to a variety of factors, including the natural anatomy, anatomical variations between patients, injury and/or spinal degradation, and desired rod curvature and/or pedicle screw placements, which can make it difficult for a surgeon to engage subsequent instruments for compression and/or distraction. Tower collision can also be exacerbated where a curved spinal rod is used to match and/or correct lordotic anatomy, potentially presenting the surgeon with a challenging rod insertion and/or alignment as well as significantly limiting the amount of "real estate" available to accommodate additional surgical instrumentation. In addition, tower collision and/or interference (see FIG. 9A) can inhibit proper screw placement and/or cause "false" set screw tightening (see gap 900 of FIG. 9C), where the construct may be misaligned and cause the set screw to cross-thread and/or prematurely lock. Such occurrence can eventually result in loosening and/or failure of the spinal construct during spinal motion and/or the patient's healing process.

Figure 9B:
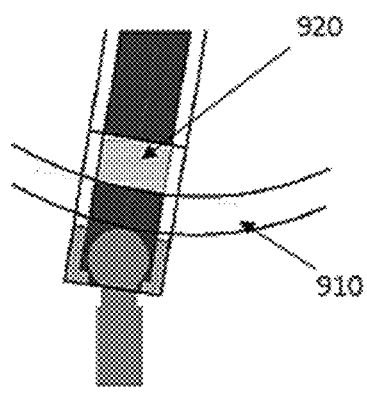
FIG. 9B depicts a correctly aligned fixation construct with set screw tightened.
Figure 9C:
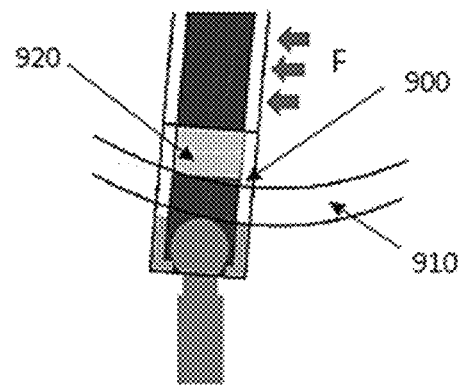
FIG. 9C depicts a misaligned fixation construct with set screw tightened.

By incorporating a flexible element in the tower that is can be capable of significant flexion (up to 360 degrees about the longitudinal axis of the tower in some embodiments), the present invention can allow proximal portions of the tower to be displaced in a desired direction and/or orientation while the remaining distal portion(s) of the tower can be attached and/or remain connected to the fixation screw in a desired manner. This arrangement desirably prevents and/or reduces the opportunity for collision and/or interference between adjacent towers, which often occurs when patient concavity of the spine is steep (i.e., small radius), making the tall tower exceed the radius of the curvature of the spine. As shown in FIG. 9B, once the fixation elements have been implanted into the spine, upon tightening the set screw the housing desirably becomes normal (i.e., perpendicular) to the rod, with the screw immovably fixed to the housing. However, where tower collision and/or interference occurs, in some cases this interference creates a force F (represented by sideways arrows in FIG. 9C) that inhibits and/or prevents the housing from assuming a normal orientation, allowing a gap 900 or other space to exist between portions of the fixation rod 910 and the set screw 920 during screw tightening, which can allow the set screw to loosen and/or other construct to fail after tower removal and/or during patient movement.

Figure 10B:
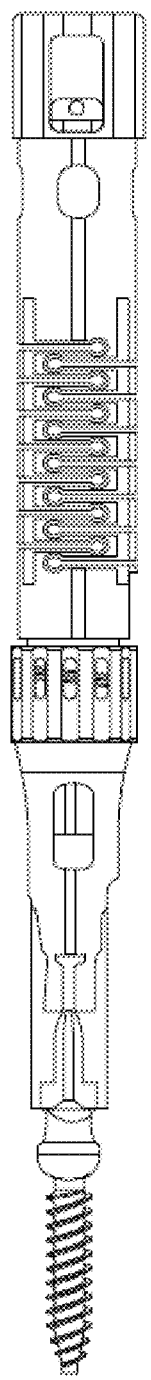

In at least one exemplary embodiment, the tower housing can be rendered flexible in one or more regions by forming slit cut patterns or any other form of material removal, which on one exemplary embodiment can be made along the tower's middle region near where the center of the curvature meets. This creation of a flexible zone can be integrated into any percutaneous pedicle screws with high towers or it would apply to any modular reduction tower or similar element (see FIGS. 10A and 10B).

Figures 11A, 11B:
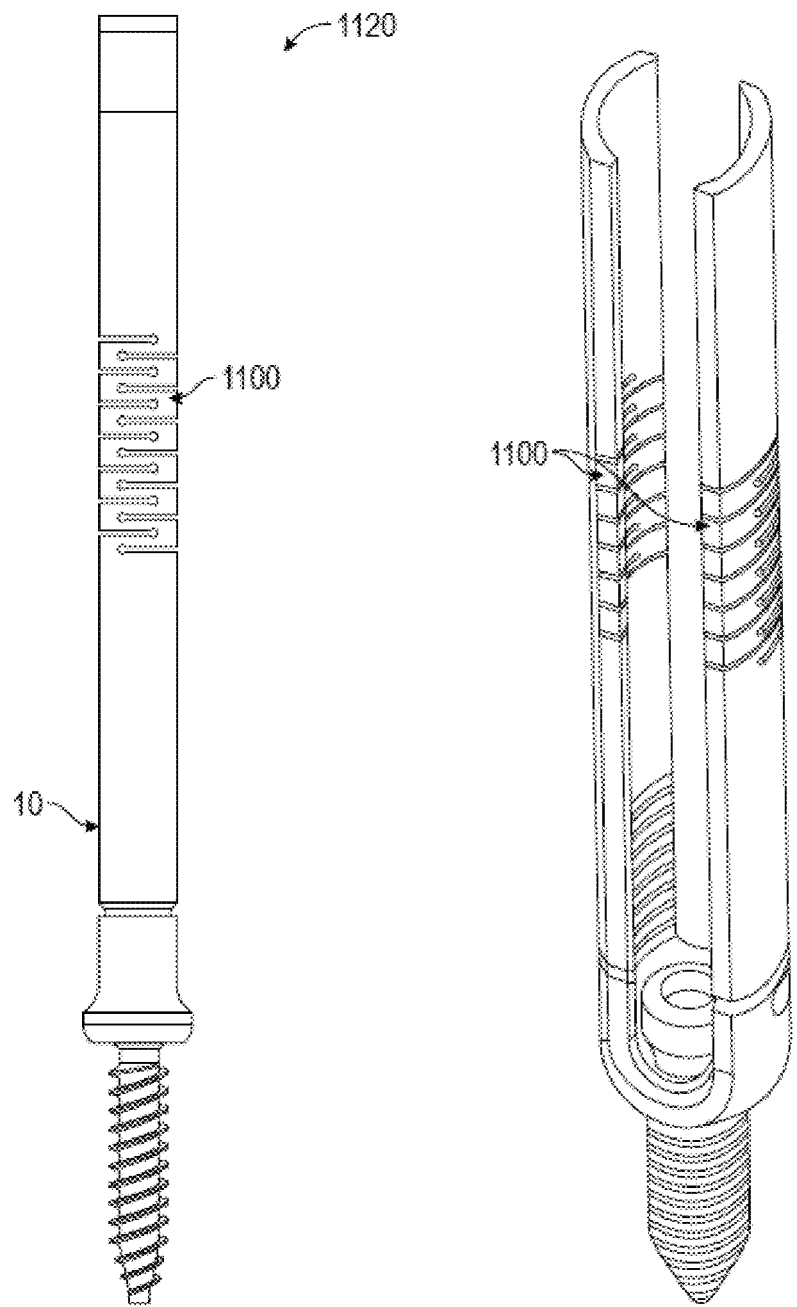
FIGS. 11A and 11B depict another embodiment of a percutaneous spinal instrument having flexible zones in accordance with the present disclosure.
Figure 12A:
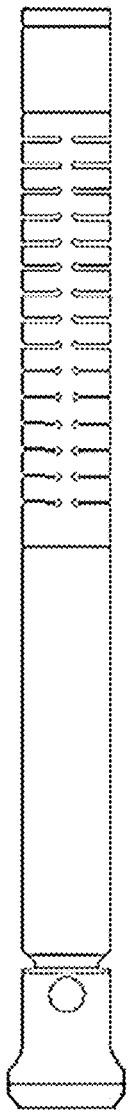
FIGS. 12A through 12C and 13A through 13F depict additional alternative embodiments of flexible regions that can be integrated into various spinal instrumentation.
Figure 12B:
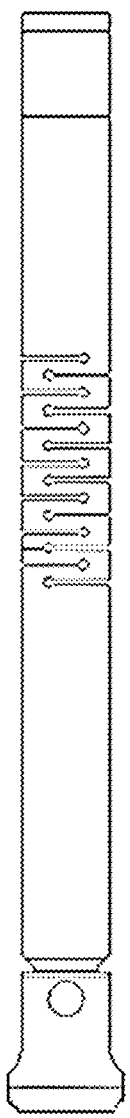
Figure 12C:
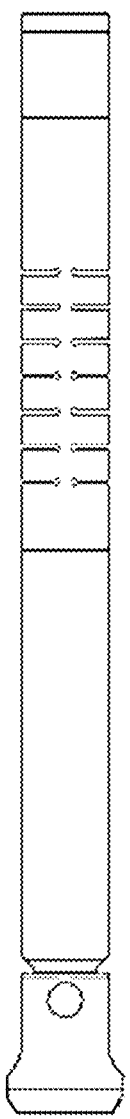
Figure 13A:
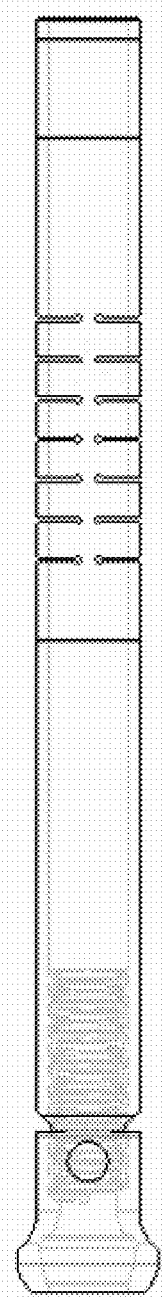
Figure 13B:
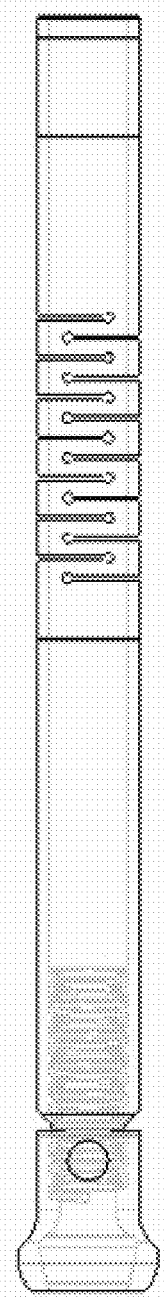
Figure 13C:
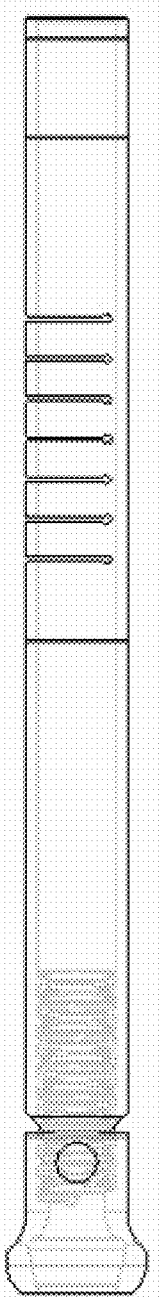
Figure 13D:
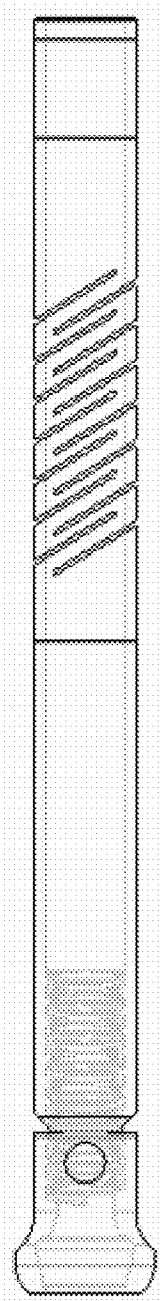
Figure 13E:
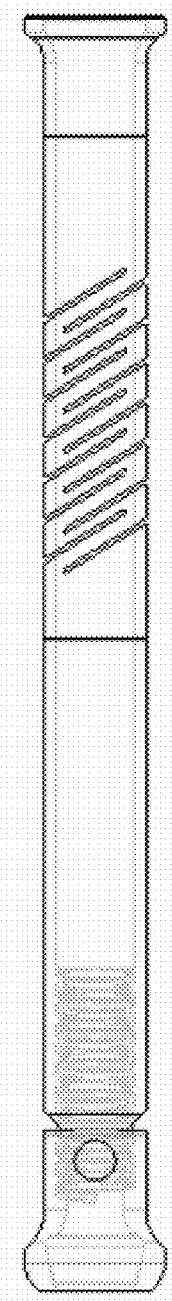
Figure 13F:
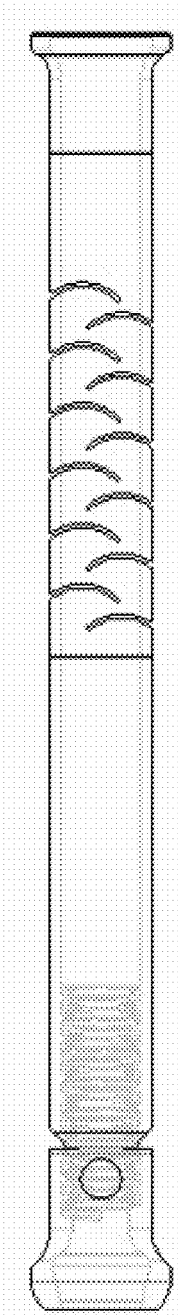

FIGS. 11A and 11B depict an alternative embodiment of rigidity reducing cuts 1100 provided on upstanding leg portions 1110 of a minimally invasive screw assembly 1120. In this embodiment, portions of the assembly 1120 can be flexed in a desired direction while continuing to provide an access path through the patient's tissues in a desired manner. In various alternative embodiments, the flexible section could comprise a section of weaker material, such as a different and/or softer material that the remainder of the assembly, or the flexible section could comprise a portion of reduced cross-section or different design of the same material that potentially leads to an increased flexibility and/or greater ductility.

FIGS. 12A through 12C and 13A through 13F depict additional alternative embodiments of flexible regions that can be formed in various spinal instrumentation. If desired, the flexible region can be designed to provide a full 360 degrees of flexion about the longitudinal axis of the tool, while other embodiments might provide flexion along only one or more axis, while inhibiting flexion along other axes. In addition, the flexion slits may completely encircle the too, or may be provided only about a portion of the circumference of the tool, such as less than 180 degrees and/or less than 90 degrees and/or less than 45 degrees of the circumference of the tool.

In various of the described non-limiting embodiments of a tower 400 having a tower lip 421 that comprises multiple tower lip segments 421' (shown in FIG. 3E), the bone fixation device 110 may be assembled by holding the base of the bone fastener 200 in one hand, and a portion of the tower body 410 at the receiving end of the tower 400 (portion A, shown in FIG. 3A) in the other hand, aligning the coupling lip segments of the coupling body 310 with the spaces 425 in the tower 400, pushing the coupling body 310 into the receiving end of the tower body 410 (portion A in FIG. 3A) and past the tower lip segments 421', and, when properly inserted, turning one or both of the tower body 410 and coupling body 310 with respect to each until the coupling lip segments substantially overlap with the tower lip segments 421'.

Once the tower 400 and bone fastener assembly 200/300 are properly assembled, such as, for example, when the channel(s) 403 (if any) of the tower body 410 is aligned with the channel 302 in the coupling body 310, a cannulated bone screw driver assembly (not shown) may be inserted in the tool channel 401. The screw driver (not shown) may be inserted through the tool channel 401 to the head of the bone fastener 200, at which point the screw driver (not shown) may be manipulated to properly seat the male (or female) end of the head of the screw driver (not shown) in the female (or male) end of the bone fastener 200. Once the screw driver head (not shown) is properly seated, an outer sleeve (not shown) of the screw driver may be rotated to tighten the screw driver with respect to the tower body 410. The cannulated bone fastener 200 may then be placed over the guide K-wire and slid through the final dilator to the pedicle. Once the bone fastener 200 reaches the vertebral body, the guide wire may be removed and the bone fastener 200 advanced to the desired depth by rotating the screw driver (not shown). The cannulated screw driver (not shown) and the final dilator may be removed at this point.

The above process may be repeated for each of the target pedicles.

After two or more of the bone fastener devices 110 have been installed, as described above, rod measurement calipers (not shown) may be used as is known in the art. The towers 400 in the bone fixation system (e.g., shown in FIG. 2) may be aligned such that the channels 302 of the coupling assemblies 300 are aligned. Also, the open channel(s) 403 and/or slots 412 may be aligned. Then, the appropriate fastener connector 120 may be selected together with an appropriate inserter tool (not shown, such as, e.g., an offset left rod inserter, an offset right rod inserter, an in-line rod inserter, or the like). The inserter tool (not shown) may be inserted in and guided through the tool channel 401 to a predetermined position in the tower body, at which point the fastener connector 120 may be deployed and placed in the channel 302 of each of the aligned coupling bodies 310. Alternatively, the inserter tool (not shown) may be delivered to the fastener connector 120 installation site(s) external to any tower 400.

If the fastener connector 120 does not fully seat in a channel 302 of a coupling body 310, standard reduction (e.g., derotation device 500 (described below), standard rod pushers (not shown), supplemental reduction (e.g., using parallel reducers (not shown))), or the like may be used to facilitate proper positioning and seating of the fastener connector 120 with respect to the channel 302.

After the fastener connector 120 is properly seated in each intended coupling body 310, then a set screw 370 may be placed on a set screw starter tool (not shown), and the set screw starter tool (not shown) with set screw 370 may be inserted in and down the tower body 410 until it reaches the upper surface of the coupling body 310, as seen in FIG. 4A. Final tightening of the set screws 370 may be carried out by using a counter torque tube holder tool (not shown) to hold the top of the tower 400, and turning the set screw tightening tool (not shown). As seen in FIG. 4B, if the pitch of the threading 379 does not match the pitch of the threading 319 in the coupling body, the set screw 370 will push down on the upper surface of the coupling body 310 and rotate until the pitch of the threading 379 matches that of the threading 319 in the coupling body 310, at which point the set screw 370 will engage and progress downward into the threading 319 in the coupling body 310 (shown in FIG. 4C).

The bone fasteners 200 should be inserted with some good force and within the confines of the vertebra, because the pedicle should be a strong pedicle and should hold the bone fastener 200 well, since this is a fastener that is going to hold the vertebra in place while the fusion is taking place. After each bone fastener 200 is secured in place, the bone fasteners 200 may be tested by running a small current through the fasteners to determine whether the fastener may irritate a nerve. The process may be repeated for each of the other fasteners.

Figure 5:
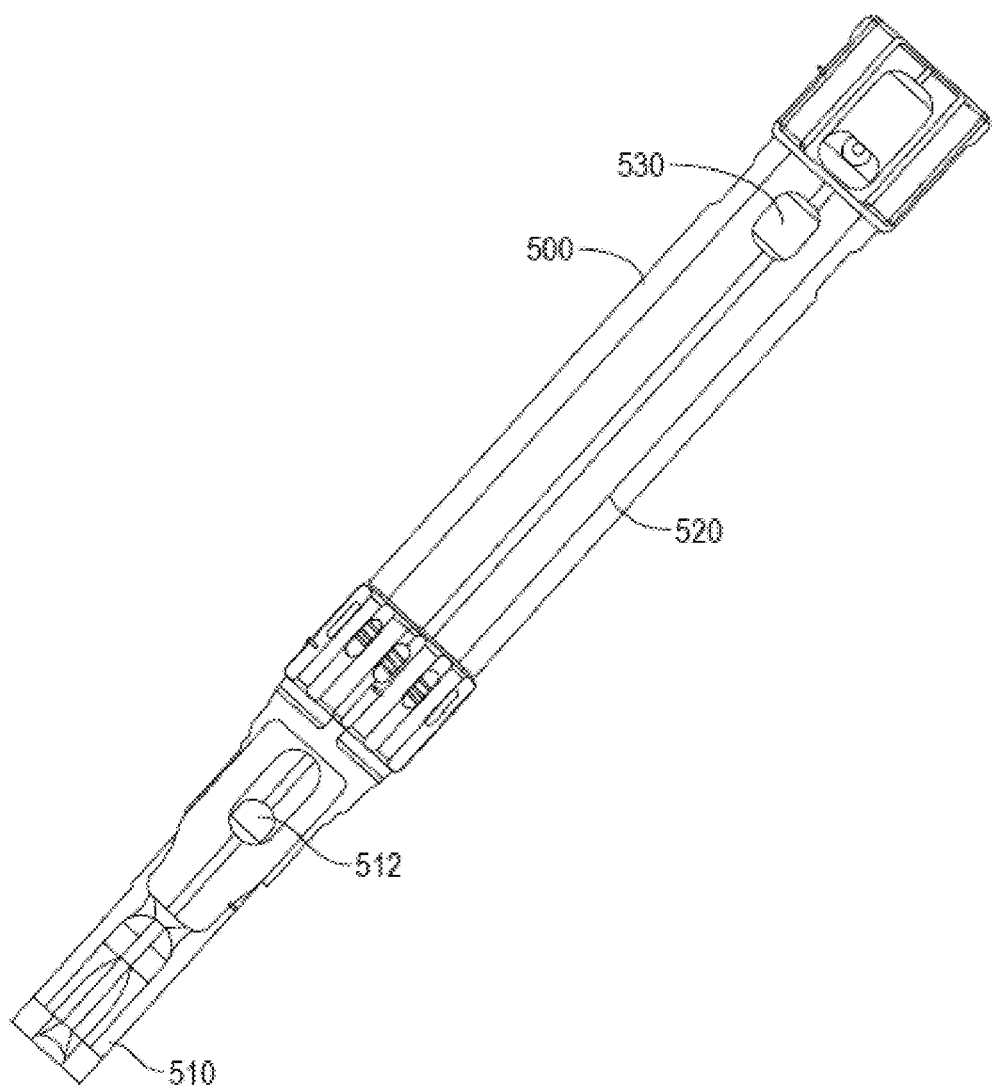
FIG. 5 shows an example of a derotation device, constructed according to the principles of the disclosure.

FIG. 5 shows an example of a derotation device 500, constructed according to the principles of the disclosure. The derotation device 500 may be used for derotation (e.g., en bloc derotation, segmental derotation, etc.), deformity correction (e.g., rib hump correction, etc.), translation, and the like. The derotation device 500 may include a reinforced cannulated shell.

Figure 6A:
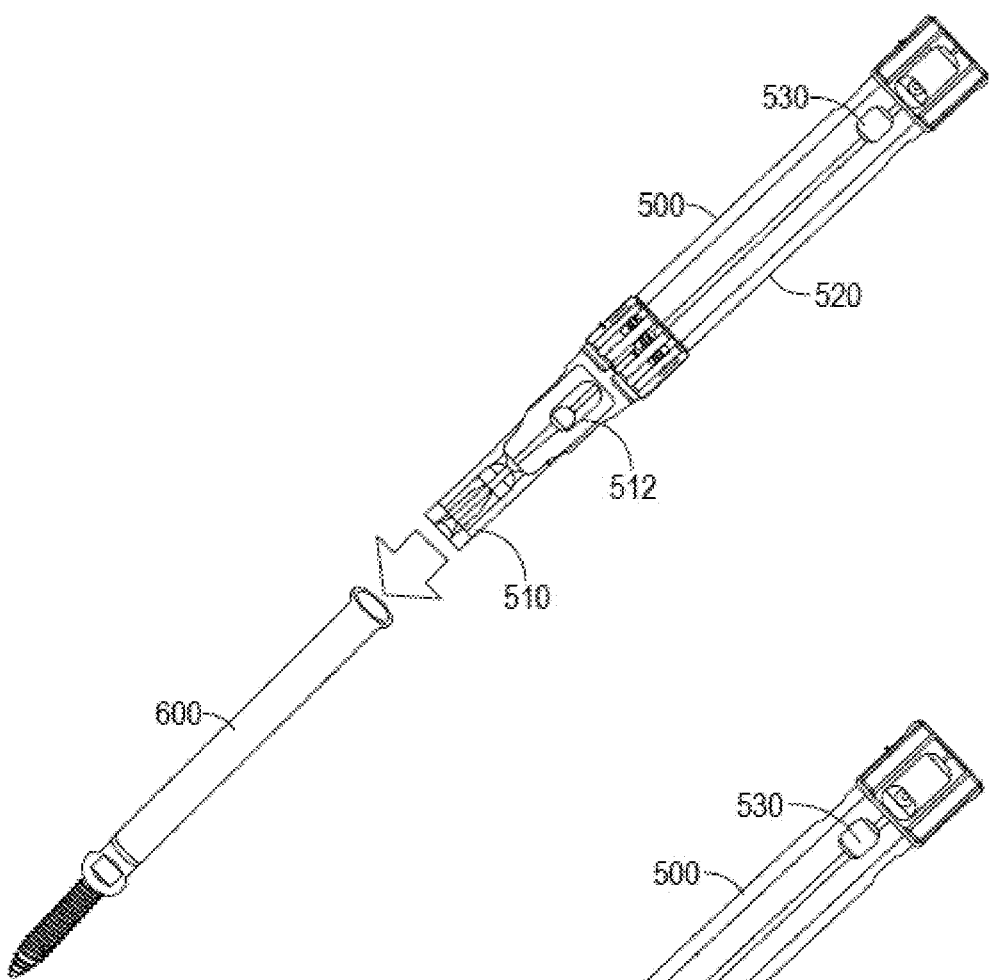
FIG. 6A shows the derotation device in FIG. 5 and a derotation tower according to the principles of the disclosure.
Figure 6B:
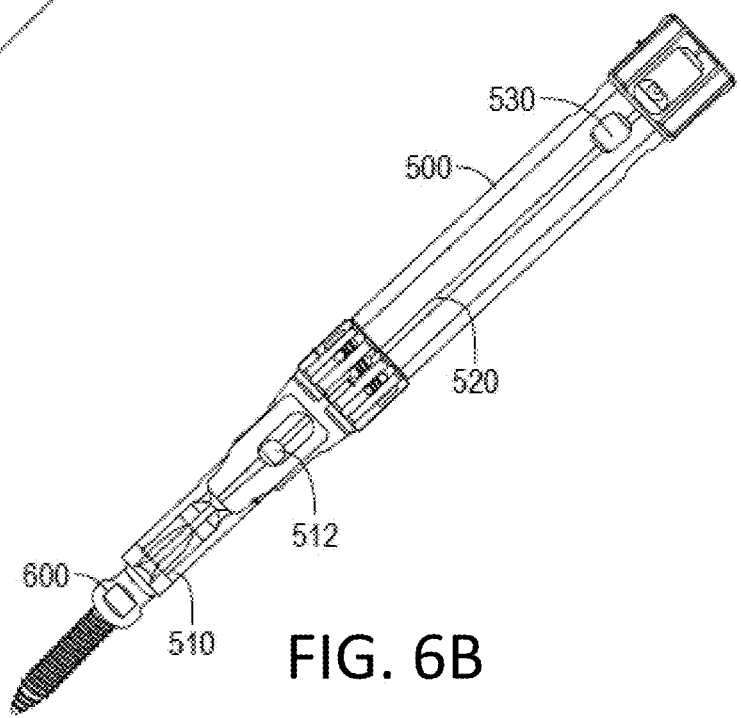
FIG. 6B shows the derotation device encapsulating the derotation tower in FIG. 6A.

As seen in FIGS. 6A and 6B, the derotation device 500 may be configured to slide over and at least partially encapsulate a modular derotation tower 600 (e.g., tower 400 of the bone fastening device 110 shown in FIGS. 2 and 3A). The derotation device 500 may have an elongated shaped housing with a hollow body structure to receive the derotation tower 600. The derotation device 500 may have an opening at a narrow tip end 510, into which the derotation tower 600 may be inserted. The derotation device 500 may also include a locking mechanism, such as, for example, sliding lock 512 or the like, which may fix the tower 600 once inserted into the derotation device 500. The derotation device 500 may also include a grip portion 520, which may have a larger diameter than the narrow tip end 510. When manually operated with a surgeon's hand, the larger grip portion 520 may increase the rotational torque, thereby allowing the derotation device 500 to function as a torque sleeve.

Figure 7:
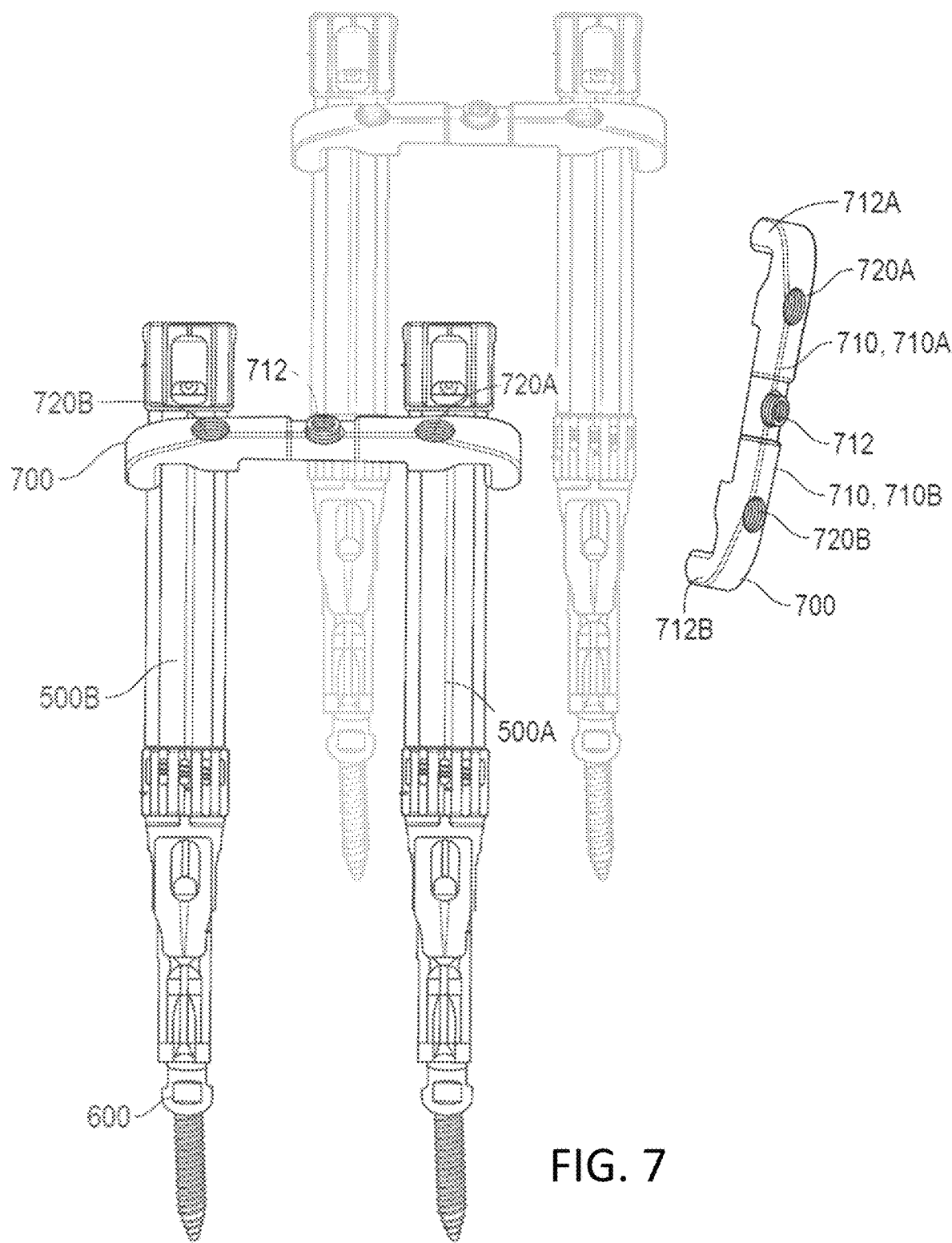
FIG. 7 shows an example of a bone fixation system, including a crosslink for linking two or more derotation devices to each other, according to the principles of the disclosure.

As seen in FIG. 7, a crosslink unit 700 may be used to fix two or more derotation devices 500A, 500B at a desired distance therebetween. The crosslink unit 700 may have an elongated body 710 having two bent ends 712A, 712B. The bent ends 712A, 712B may attach to the derotation devices 500A, 500B, respectively. For example, the body 710 may have a pair of set screws 720A, 720B. As seen in FIG. 5, the derotation devices 500A, 500B may include a screw hole 530 (not shown in FIG. 7) near the top end portion thereof Referring to FIG. 7, the derotation device 500A may be placed to contact an inner bent surface of the bent end 712A, and then the set screw 720A may be screwed into the screw hole 530 of the derotation device 500A, which may fix the derotation device 500A to the ben end 712A of the crosslink unit 700. The derotation device 500B may be fixed to the opposite bent end 712B of the crosslink unit 700 in a similar manner.

A length of the crosslink unit 700 may be adjustable. For example, the body part 710 may be divided into two parts: first body part 710A and second body part 710B, which are fixed to each other by a set screw 712. To adjust the length, the set screw 712 may be unscrewed to disengage the first and second body parts 710A, 710B from each other. Then first and second body parts 710A, 710B may then be pulled away from each other or pushed toward each other to increase or decrease the length of the body 710, respectively. Once the body 710 is adjusted to a desired length, the set screw 712 may be screwed to fix the first and second body parts 710A, 710B together.

Referring to FIGS. 3A-3E, 4A-4C, 5, 6A, 6B and 7 simultaneously, the bone fixation (or stabilization) system 100, the derotation device 500, the crosslink unit 700 may be configured for use in, for example, anterior approach and discectomy applications. For instance, after a patient is positioned in a prone or supine position on, for example, a radiolucent operating table, the surgical area cleaned, incisions made, muscle tissue and/or organs moved to the side(s), and other common surgical procedures carried out, and the bone fixation system 100 installed as described above, an individual derotation device(s) 500 (or two or more derotation devices 500 when connected by one or more cross link units 700) may be manipulated by a surgeon's hand, to allow for rotational and/or axial adjustment of the derotation device(s) 500.

Figure 14A:
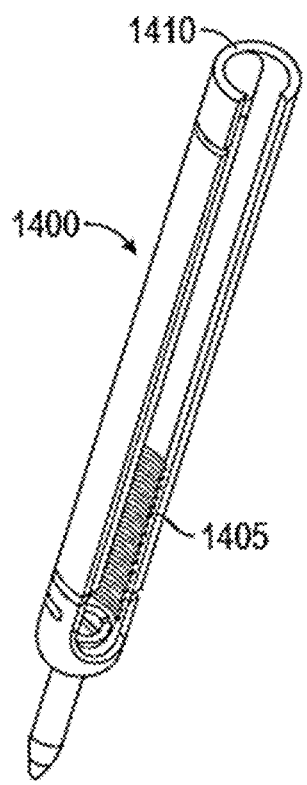
FIGS. 14A through 14C depict additional alternative embodiments of flexible towers.
Figure 14B:
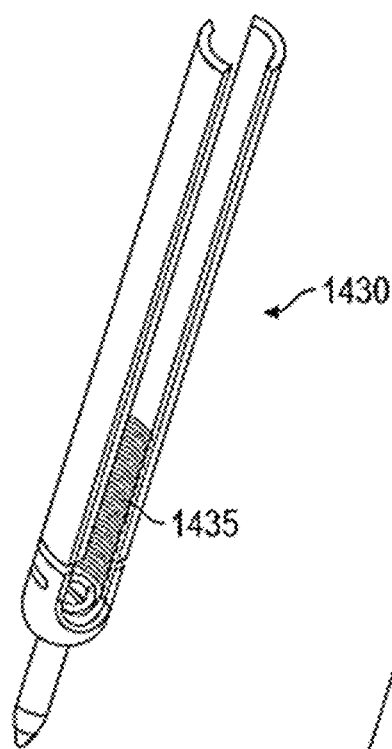
Figure 14C:
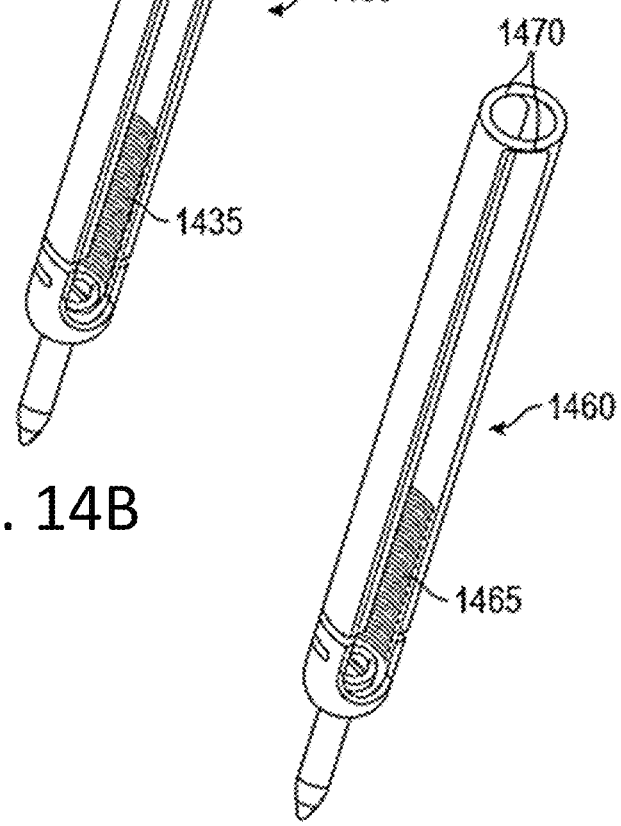
Figure 15A:
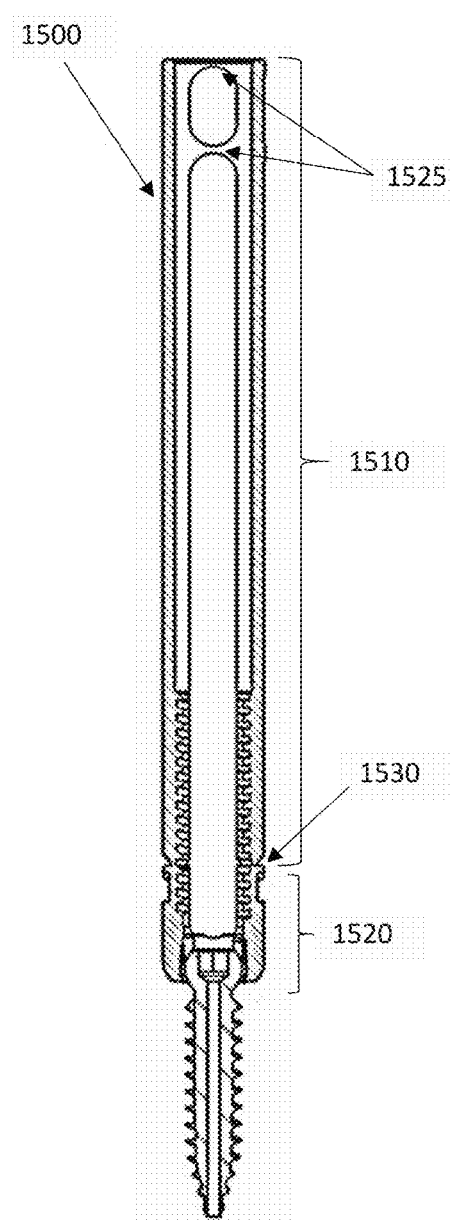
FIGS. 15A through 15D depict an additional embodiment of a tower body that includes a tubular body portion with an integrated detachable tip portion.
Figure 15B:
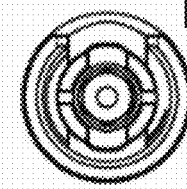
Figure 15C:
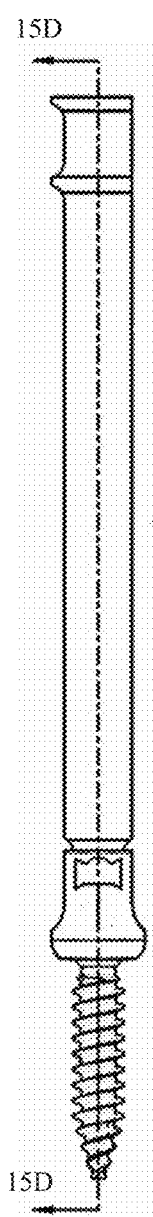
Figure 15D:
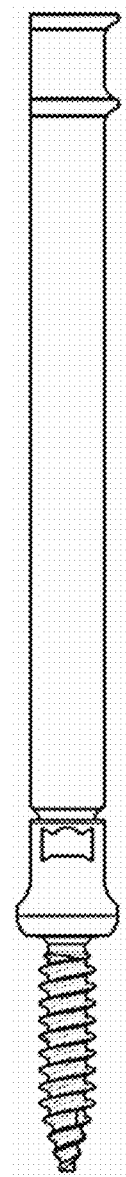

FIGS. 14A through 14C depict additional embodiments of tower bodies 1400, 1430 and 1460 which can incorporate flexible regions 1405, 1435 and 1465 as described herein. As best seen in FIGS. 14A and 14C, the towers 1400 and 1460 can further include a single proximal bridge 1410, or a pair of proximal bridges 1470 (or various other numbers and/or locations of bridges, including three, four or more bridges and/or pairs of bridges), which can desirably increase the strength and stability of the tower during use, including during alignment of the fixation elements and/or flexion of the towers.

FIGS. 15A through 15D depict one exemplary embodiment of a tower body 1500 that includes a tubular body portion 1510 with an integrated tip portion 1520. If desired, the tube body 1510 can include a flexible section (not shown) along virtually any portion of its length, which may include flexible sections at different points along each wall of the tube body, if desired. The tube body 1510 also can include one or more bridge portions 1525. In this embodiment, the integrated tip portion 1520 is attached to the tube body at a reduced diameter section 1530, which desirably forms a "weakened" and/or frangible link between the tube body 1510 and the tip portion 1520. Desirably, this arrangement will allow the tip portion 1520 to be separated from the tube body 1510 at a desired point in the surgery, with the tip portion capable of function as a polyaxial or other type head of the pedicle screw assembly.

FIGS. 16A through 16C depict another exemplary embodiment of a tower body 1600 that includes a tubular body portion 1610 with an integrated tip portion 1620, along with a single bridge portion 1625. As similarly described in combination with any of the embodiments described herein, the tube body 1610 can include a flexible section (not shown) along virtually any portion of its length, which may include flexible sections at different points along each wall of the tube body, if desired.

Figure 17:
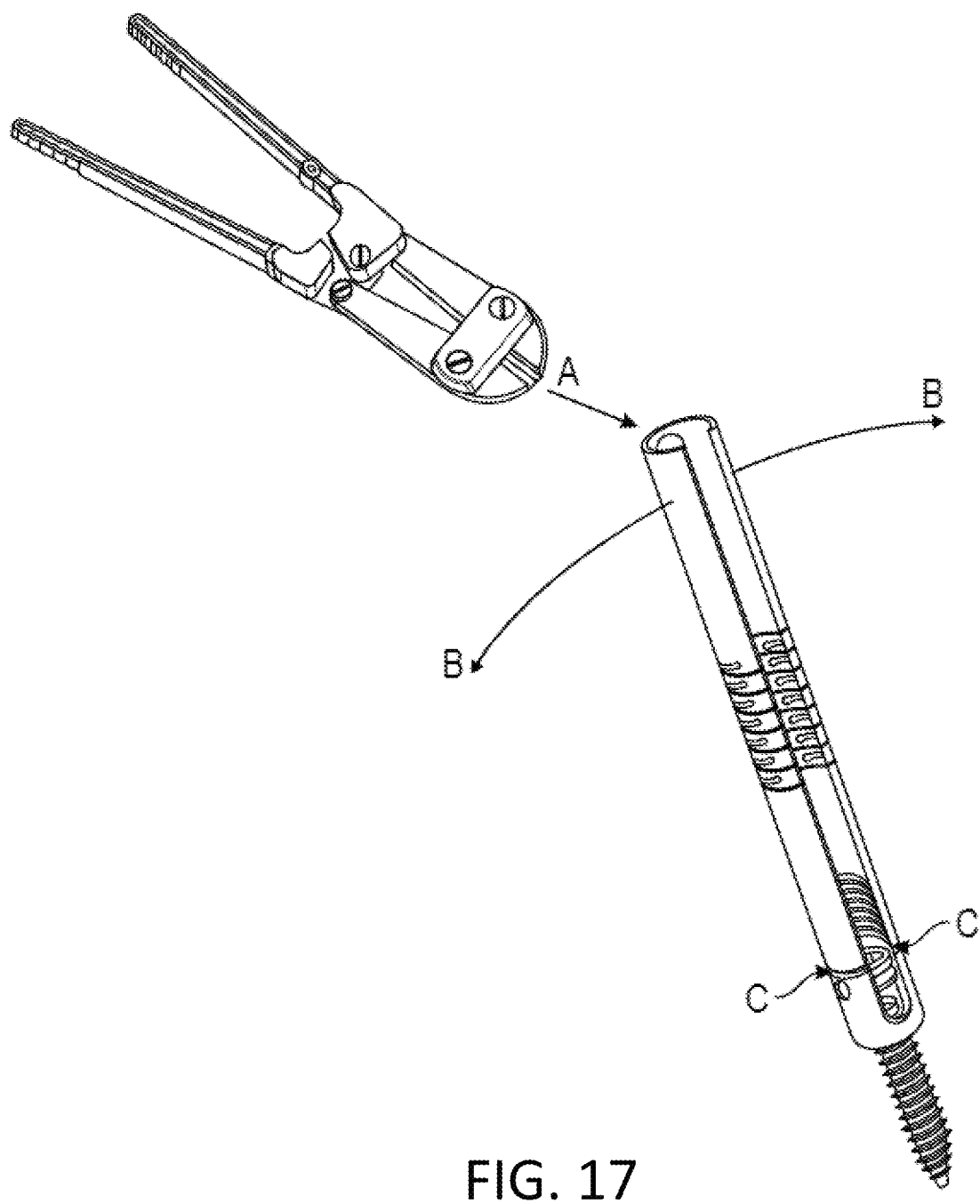
FIG. 17 depicts one exemplary method of removing a tubular body portion from a tip portion of a tower body.
Figure 19A:
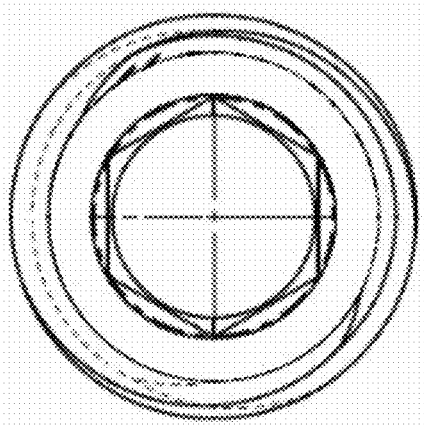
FIG. 19A through 19D depict various views of a set screw for use with various embodiments of the present invention.
Figure 19B:
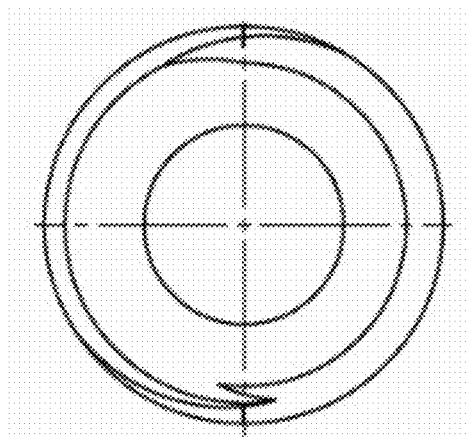
Figure 19C:
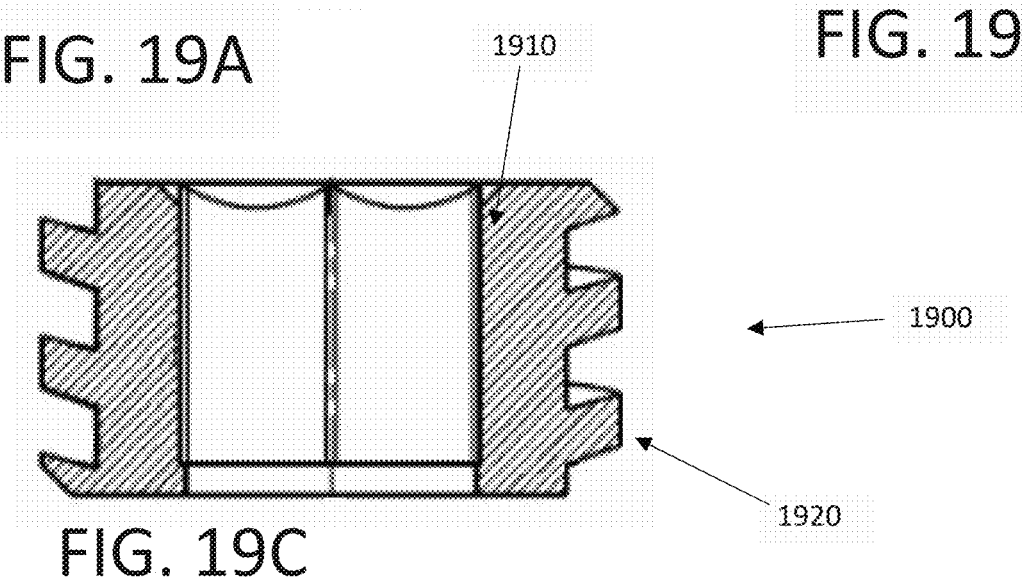
Figure 19D:
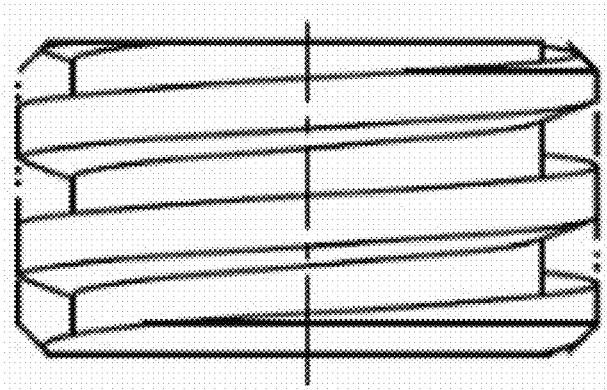

In various embodiments, once one or more of the individual fixation elements (i.e., the pedicle screws) are secured into the targeted anatomy in desired positions and/or orientations (which may include the placement of connecting rods and/or set screws, one or more of the tower bodies may be removed from the tip portions. For example, FIG. 17 depicts one exemplary method of removing a tubular body portion 1710 from a tip portion 1720 of a tower body 1700. In this embodiment, the bridge portion 1725 of the tower body 1700 can be severed ("A") by a metal cutter 1790 or other surgical tool, and the individual sections 1740 and 1745 of the body portion 1710 can be flexed ("B") and/or otherwise displaced, which desirably stresses, "works" and/or breaks the frangible link 1750 ("C"), leaving the tip portion 1720 within the anatomy while allowing the individual sections 1740 and/or 1745 to be removed. Where a flexible section (not shown) has been incorporated into the individual sections 1740 or 1745, a tubular tool or surgical pliers can be utilized to flex a portion of the individual sections 1740 and/or 1745 below the flexible section to break the frangible link in a desired manner.

FIGS. 18A and 18B depict front plan and cross-sectional views, respectively, of one embodiment of an exemplary fixation element 1800 incorporating a tip portion 1810 which engages with a bone fastener in the form of a polyaxial pedicle screw 1820. When fully assembled, the tip portion 1810 holds a head portion 1830 of the polyaxial pedicle screw, which can be sandwiched between a first inner ring 1840 and a second inner ring 1850, with the inner rings designed and positioned such that when a force is applied in a downward direction by a set screw 1890 (e.g., a force that is substantially perpendicular to the plane of the upper surface of the inner ring), the volume of the cavity that holds the head portion 1830 of the bone fastener and/or a fixation rod 1880 is compressed or reduced, thereby securely engaging and holding the head portion 1830 of the bone fastener and the rod 1880 by the inner walls of the tip portion 1810 and the rings.

FIG. 19A through 19D depict various views of a set screw 1900 for use with various embodiments of the present invention. The set screw 1900 can include a central body 1910 with externally positioned threads 1920. In various embodiments, the threads can include a sawtooth or reverse thread pattern, as well as square threads and/or other thread designs to desirably reduce and/or obviate splay of the tip portion, if desired.

The terms "including," "comprising," and variations thereof, as used in this disclosure, mean "including, but not limited to," unless expressly specified otherwise.

The terms "a," "an," and "the," as used in this disclosure, means "one or more," unless expressly specified otherwise.

Devices that are in communication with each other need not be in continuous communication with each other, unless expressly specified otherwise. In addition, devices that are in communication with each other may communicate directly or indirectly through one or more intermediaries.

Although process steps, method steps, or the like, may be described in a sequential order, such processes and methods may be configured to work in alternate orders. In other words, any sequence or order of steps that may be described does not necessarily indicate a requirement that the steps be performed in that order. The steps of the processes or methods described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure.

What is claimed is:

1. A bone fixation system, comprising:
a bone fastener having an externally threaded shank and a generally spherical head;
a tower having a tower body including a plurality of tower walls, each of the tower walls including at least one flexible section positioned between a first rigid section and a second rigid section, the first rigid section of each of the tower walls forming a rigid first tower body section and the second rigid section of each of the tower walls forming a rigid second tower body section, each of the at least one flexible sections comprising a first set of vertically stacked slits extending substantially transverse across a majority of a width of each of the tower walls and a second set of vertically stacked slits extending substantially transverse across a majority of the width of each of the tower walls, the first set of the plurality of vertically stacked slits being laterally offset from the second set of the plurality of vertically stacked slits, wherein the plurality of tower walls are separated by at least one tower channel, the vertically stacked slits each having a first end and a second end, the first end of the vertically stacked slits opening into the at least one tower channel and the second end of the vertically stacked slits including an enlarged opening, each of the plurality of tower walls having a first end proximate to a frangible linkage and an opposing second end proximate to at least one severable bridge element which extends across the tower channel between the plurality of tower walls;
a connection element attached to the substantially rigid second tower body section by the frangible linkage, the connection element having a distal opening sized to accommodate the shank of the bone fastener, the connection element further having an internal threadform formed on an inner surface therein; and
a set screw having an external set screw thread configured to mate with the internal threadform of the connection element.

2. The bone fixation system of claim 1, wherein the bone fastener comprises a polyaxial pedicle screw, with the shank extending from the head.

3. The bone fixation system of claim 1, wherein the connection element further comprises a cavity that receives and holds the head of the bone fastener.

4. The bone fixation system of claim 1, wherein the connection element further comprises a fastener connector receiving channel formed by a pair of upper inner walls.

5. The bone fixation device of claim 4, further comprising a fastener connector having a portion that seats within the fastener connector receiving channel.

6. The bone fixation system of claim 1, wherein at least a portion of the tower body further comprises an internal tower thread.

7. The bone fixation system of claim 6, wherein the internal threadform of the connection element mates with the internal tower thread.

8. The bone fixation system of claim 1, wherein the at least one flexible section of each tower wall is located proximal to a midpoint of the tower body.

9. The bone fixation system of claim 1, wherein the connection element further comprises at least one inner ring which engages with the generally spherical head of the bone fastener.

10. The bone fixation system of claim 1, wherein the at least one tower channel comprises a longitudinally extending channel extending across the frangible linkage.

11. A bone fixation system, comprising:
a bone fastener having an externally threaded shank and a generally spherical head;
a tower having a tower body with a pair of tower walls extending along a longitudinal tower axis of the tower body forming a tubular internal access pathway, each of the tower walls having at least one flexible section positioned between a first rigid section and a second rigid section, the first rigid section of each of the tower walls forming a first rigid tubular section of the tower body having a first longitudinal axis, the second rigid section of each of the tower walls forming a second rigid tubular section of the tower body having a second longitudinal axis, the first and second longitudinal axes being generally parallel, the at least one flexible section of each tower wall comprising a plurality of longitudinally spaced transverse slots formed partially through the tower wall wherein in each flexible section, a first set of the plurality of longitudinally spaced transverse slots partially overlaps a second set of the plurality of longitudinally spaced transverse slots to allow the flexible section to deform in an arcuate shape and cause the first longitudinal axis to be positioned non-parallel to the second longitudinal axis, the plurality of longitudinally spaced transverse slots each having a generally uniform width with an enlarged distal tip, at least a portion of the tower body including an internal tower thread;

a connection element attached to the tower body by a frangible linkage, the connection element having a distal opening sized to accommodate the shank of the bone fastener, the connection element further having an internal threadform formed on an inner surface therein, the internal threadform extending across the frangible linkage and mating with the internal tower thread; and a set screw having an external set screw thread configured to mate with the internal threadform of the connection element;

wherein the first and second tower walls are separated by a pair of opposing tower channels, the first rigid section of each of the tower walls further comprising a first severable bridge element extending from the first tower wall to the second tower wall across at least one of the pair of opposing tower channels.

12. The bone fixation system of claim 11 wherein the bone fastener comprises a polyaxial pedicle screw, with the shank extending from the head.

13. The bone fixation system of claim 11 wherein the connection element further comprises a cavity that receives and holds the head of the bone fastener.

14. The bone fixation system of claim 11 wherein the connection element further comprises a channel formed by a pair of upper inner walls.

15. The bone fixation device of claim 14, further comprising a fastener connector having a portion that seats within the channel of the connection element.

16. The bone fixation system of claim 11, wherein the tower further comprises a second severable bridge element extending across extending across a second tower channel of the pair of opposing tower channels.

17. The bone fixation system of claim 11, further comprising a connection rod which extends transversely through at least one of the pair of opposing channels.

18. The bone fixation system of claim 11, wherein the external set screw thread of the set screw mates with the internal threadform of the connection element before the frangible linkage is severed.

19. A bone fixation system comprising:
an elongated tower body having a longitudinal axis, the elongated tower body having at least one flexible section positioned between an upper rigid tower section having an upper section longitudinal axis and a lower rigid tower section having a lower section longitudinal axis, the upper rigid tower section comprising first and second rigid tower wall sections separated by at least two channels with a proximal bridge extending from the first rigid tower wall section across at least one of the two channels to the second rigid tower wall section;

a screw head housing element attached to the tower body by a frangible linkage, the screw head housing element having a distal opening an internal threadform formed on an inner surface therein and a fastener connector receiving channel, the fastener connector receiving channel having a longitudinal channel axis;

the at least one flexible section comprising a plurality of substantially transverse staggered slots formed in the elongated tower body which deform the at least one flexible section along a circular arc under a lateral load to permit the upper rigid tower section to be flexed along a plane substantially parallel to the longitudinal channel axis such that the upper section longitudinal axis can be positioned non-parallel to the lower section longitudinal axis.

20. The bone fixation system of claim 19, wherein the screw head housing element further comprises at least one internal bushing with a cavity.

21. The bone fixation system of claim 19, wherein at least one of the plurality of substantially transverse staggered slots includes a proximal end which opens into at least one of the two channels and an enlarged distal tip.

22. The bone fixation system of claim 19, wherein the fastener connector receiving channel is configured to accept a connecting rod having a portion that seats within the fastener connector receiving channel.

23. The bone fixation system of claim 19, wherein at least a portion of the tower body further comprises an internal tower thread.

24. The bone fixation system of claim 23, wherein the internal threadform of the screw head housing element mates with the internal tower thread.

25. The bone fixation system of claim 19, wherein the at least one flexible section permits lateral movement of the upper rigid tower section along the plane substantially parallel to the longitudinal channel axis but which inhibits lateral movement of the upper rigid tower section away from the longitudinal axis along a second axis not substantially parallel to the longitudinal channel axis.

26. The bone fixation system of claim 19, wherein the screw head housing element further comprises at least one internal bushing.

27. The bone fixation system of claim 19, wherein the at least two channels are substantially aligned with and connected to the fastener connector receiving channel across the frangible linkage.

\* \* \* \* \*